(12) United States Patent
Chanda et al.

(10) Patent No.: US 10,113,955 B2
(45) Date of Patent: Oct. 30, 2018

(54) GAS CELL FOR ABSORPTION SPECTROSCOPY

(71) Applicants: Unisearch Associates Inc., Concord (CA); Unisearch Instruments Nanjing Inc., Nanjing (CN)

(72) Inventors: Alak Chanda, Brampton (CA); Shimin Wu, Nanjing (CN)

(73) Assignees: Unisearch Associates Inc., Concord, Ontario (CA); Unisearch Instruments Nanjing Inc., Nanjing (CN)

(*) Notice: Subject to any disclaimer, the term of this patent is extended or adjusted under 35 U.S.C. 154(b) by 0 days.

(21) Appl. No.: 15/358,781

(22) Filed: Nov. 22, 2016

(65) Prior Publication Data
US 2017/0146451 A1 May 25, 2017

Related U.S. Application Data

(60) Provisional application No. 62/267,709, filed on Dec. 15, 2015.

(30) Foreign Application Priority Data

Nov. 25, 2015 (CN) .......................... 2015 1 8315786

(51) Int. Cl.
  *G01N 21/00* (2006.01)
  *G01N 21/3504* (2014.01)
  (Continued)

(52) U.S. Cl.
  CPC ..... *G01N 21/3504* (2013.01); *G01N 21/0303* (2013.01); *G01N 21/0332* (2013.01);
  (Continued)

(58) Field of Classification Search
  CPC ............... G01N 21/25; G01N 21/3504; G01N 21/0303; G01N 21/0332; G01N 21/255;
  (Continued)

(56) References Cited

U.S. PATENT DOCUMENTS 3,916,185 A  10/1975 Jehly
4,180,739 A  12/1979 Abu-Shumays
(Continued)

FOREIGN PATENT DOCUMENTS

CA  2886213 A1  5/2015
EP  1 647 820 A2  4/2006
(Continued)

OTHER PUBLICATIONS

Altmann, R. et al., "Two-mirror multipass absorption cell," Applied Optics, vol. 20, No. 6, pp. 995-999 (Mar. 15, 1981).
(Continued)

*Primary Examiner* — Jamil Ahmed
(74) *Attorney, Agent, or Firm* — Foley & Lardner LLP

(57) ABSTRACT

Gas cells and systems for absorption spectroscopy, and methods thereof. The method involves providing a channel with an inlet for receiving a gas sample and an outlet for releasing the gas sample from the gas cell; providing first and second end components with an optically transparent portion, each of the end components is configured to minimize a difference between a temperature of the optically transparent portions and an internal temperature of the channel; mounting the first end component the channel so that the optically transparent portion is positioned for receiving an incident beam into the channel; and mounting the second end component to the channel opposite from the first end component so that the optically transparent portion is positioned for permitting optical transmission into and out of the channel.

15 Claims, 11 Drawing Sheets

(51) Int. Cl.
*G01N 21/25* (2006.01)
*G01N 21/61* (2006.01)
*G01N 21/03* (2006.01)
*G01J 3/42* (2006.01)
*G01N 21/15* (2006.01)

(52) U.S. Cl.
CPC .......... *G01N 21/255* (2013.01); *G01N 21/61* (2013.01); *G01J 3/42* (2013.01); *G01N 21/031* (2013.01); *G01N 2021/0389* (2013.01); *G01N 2021/158* (2013.01)

(58) Field of Classification Search
CPC .............. G01N 21/61; G01N 21/031; G01N 2021/0389; G01N 2021/158; G01J 3/42; G02F 1/133632
See application file for complete search history.

(56) References Cited

U.S. PATENT DOCUMENTS

| | | | |
|---|---|---|---|
| 5,178,966 A * | 1/1993 | Gillery | C03C 17/36 428/623 |
| 5,223,716 A | 6/1993 | Rossiter | |
| 5,723,864 A | 3/1998 | Atkinson et al. | |
| 5,940,180 A | 8/1999 | Ostby | |
| 6,359,671 B1 * | 3/2002 | Abileah | G02F 1/133632 349/118 |
| 6,486,474 B1 | 11/2002 | Owen et al. | |
| 6,717,665 B2 | 4/2004 | Wagner et al. | |
| 8,358,417 B2 | 1/2013 | Feitisch et al. | |
| 8,674,306 B2 | 3/2014 | Falk et al. | |
| 8,848,192 B2 | 9/2014 | Carmignani et al. | |
| 2002/0158202 A1 | 10/2002 | Webber et al. | |
| 2004/0095579 A1 | 5/2004 | Bisson et al. | |
| 2005/0286054 A1 | 12/2005 | Chen et al. | |
| 2006/0263256 A1 | 11/2006 | Koshel et al. | |
| 2007/0242720 A1 | 10/2007 | Eckles et al. | |
| 2014/0204382 A1 | 7/2014 | Christensen | |
| 2015/0160126 A1 | 6/2015 | Carangelo | |

FOREIGN PATENT DOCUMENTS

| | | | |
|---|---|---|---|
| EP | 2 108 937 A1 | 10/2009 | |
| EP | 2108937 A1 * | 10/2009 | ......... G01N 21/0332 |
| JP | 2002-040319 A | 2/2002 | |
| WO | WO-2012/142549 A1 | 10/2012 | |

OTHER PUBLICATIONS

Barlome, R., et al., "High-temperature multipass cell for infrared spectroscopy of heated gases and vapors," Review of Scientific Instruments, American Institute of Physics, vol. 78, Issue 013110, pp. 1-6 (Jan. 22, 2007).

Borysow, Jacek, et al., "Laser Multipass system with interior cell configuration," Applied Optics, Optical Society of America, vol. 50, Issue No. 30, pp. 5812-5815 (Oct. 20, 2011).

Canadian Office Action, Canadian Patent Application No. 2,886,213 (dated Jul. 2, 2015).

Extended European Search Report, European App. No. 15169283.7, Unisearch Associates Inc., et al., 8 pages (dated Feb. 10, 2016).

McManus, J.B. et al., "Astigmatic mirror multipass absorption cells for long-path-length spectroscopy," Applied Optics, vol. 34, No. 18, pp. 3336-3348 (Jun. 20, 1995).

Extended European Search Report, App. No. 16200350.3, Unisearch Associates Inc. et al., 11 pages (dated Apr. 5, 2017).

European Examination Report, App. No. 15169283.7, Unisearch Associates Inc. et al., 5 pages (dated Dec. 20, 2017).

* cited by examiner

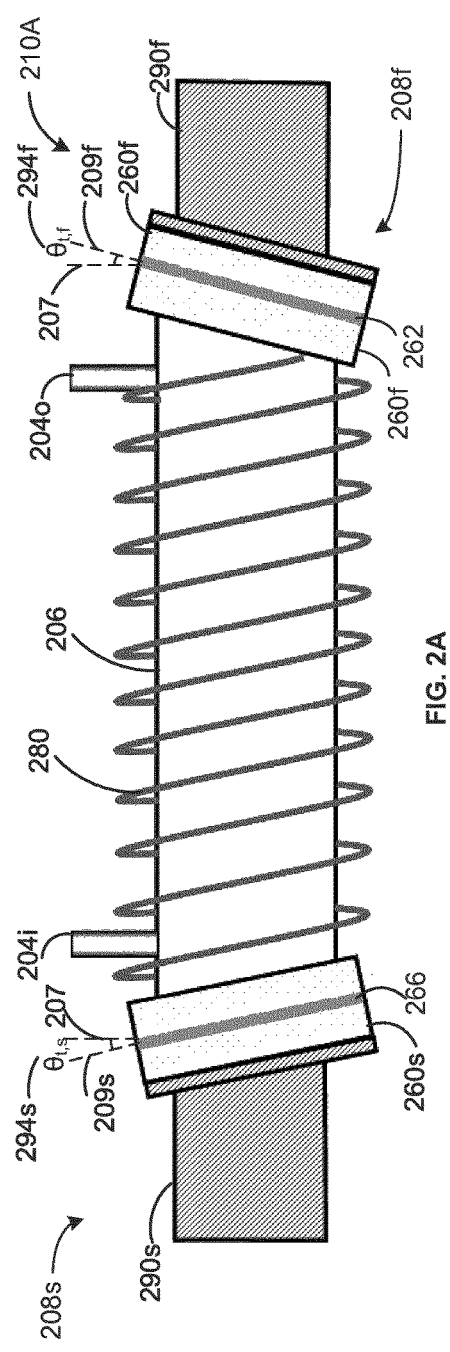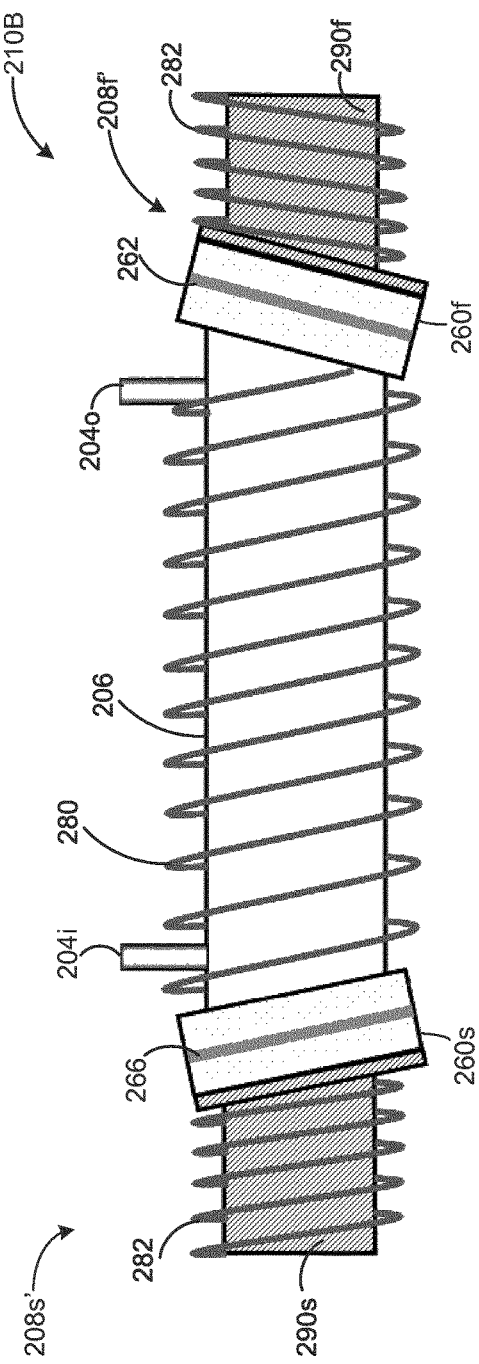

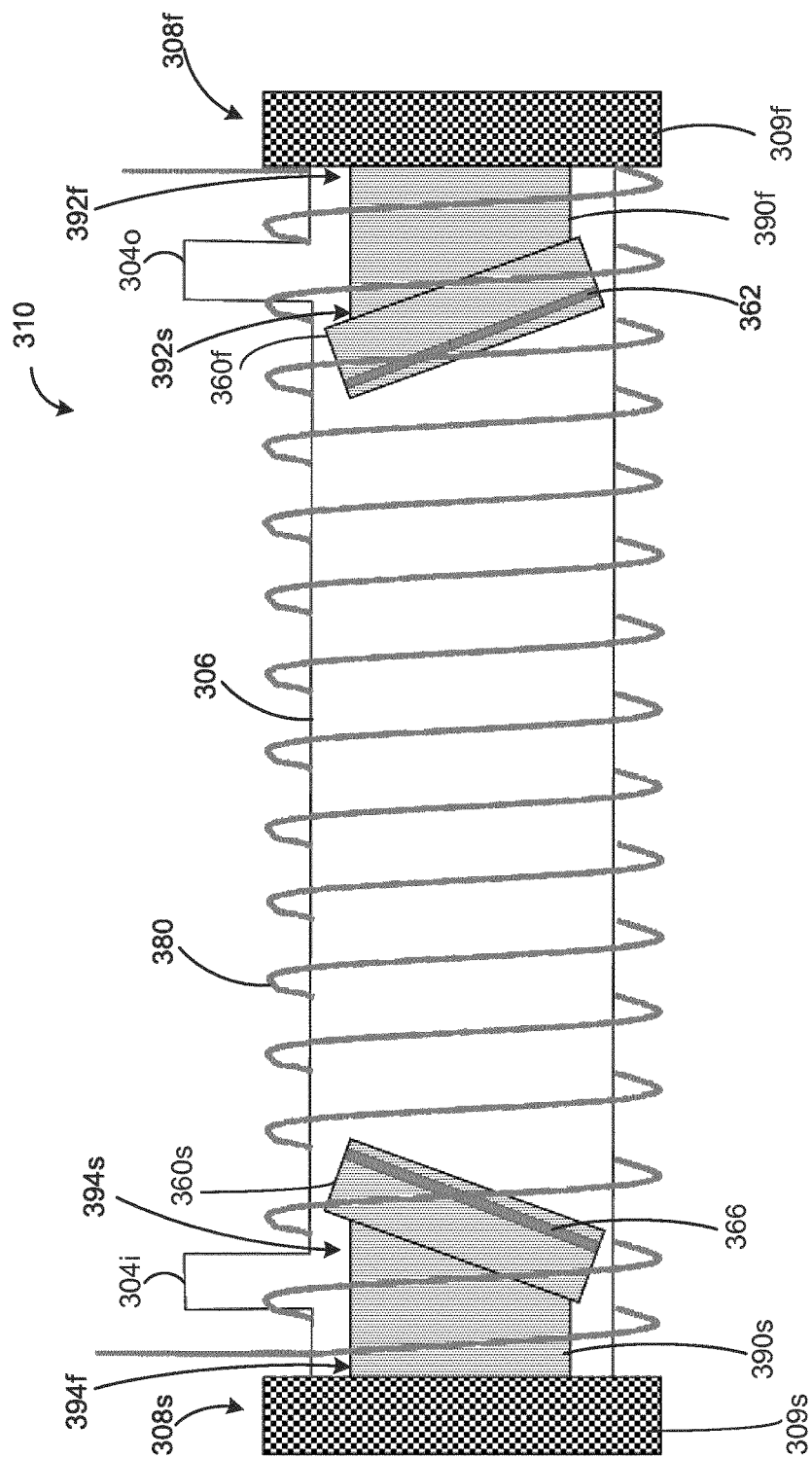

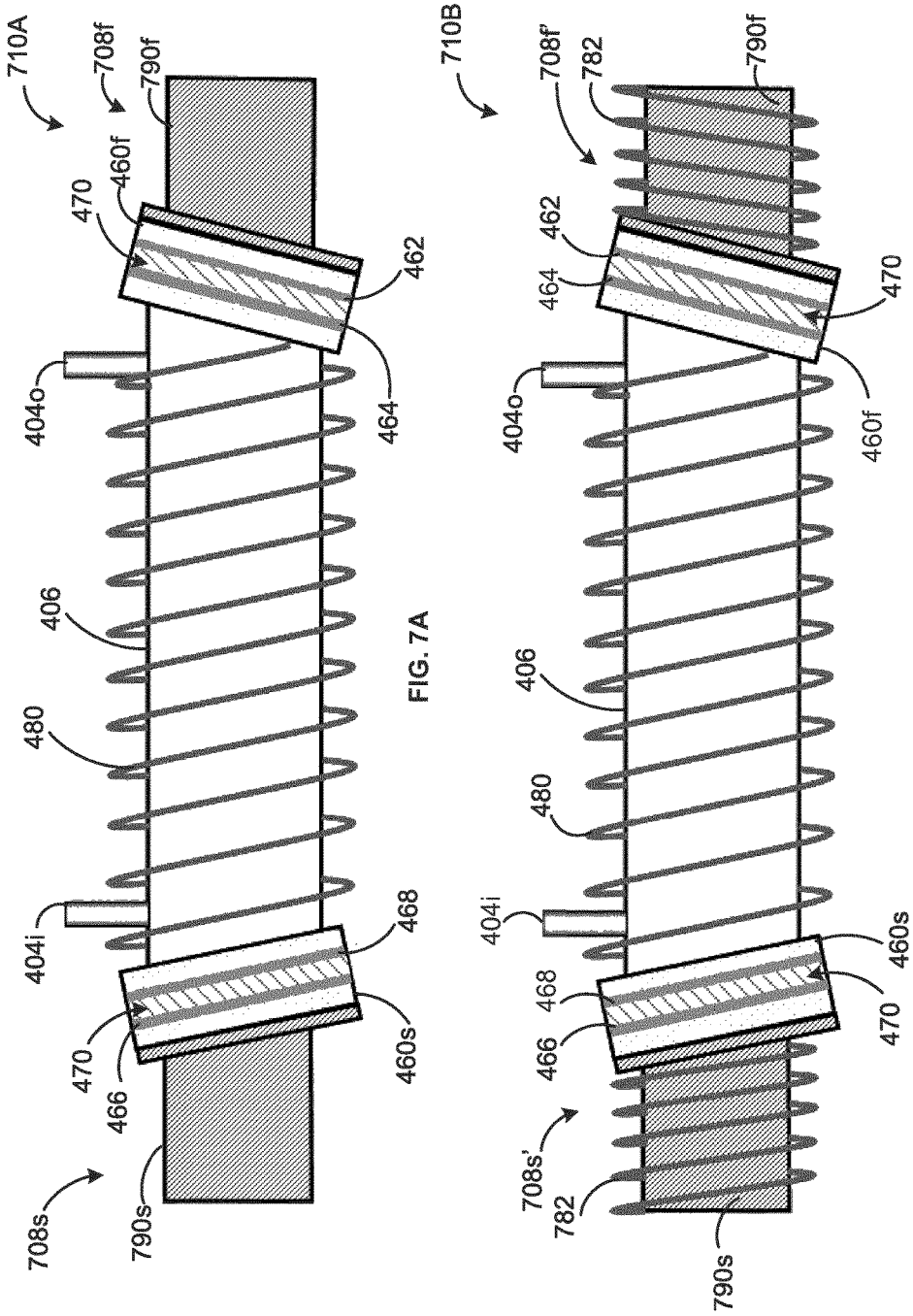

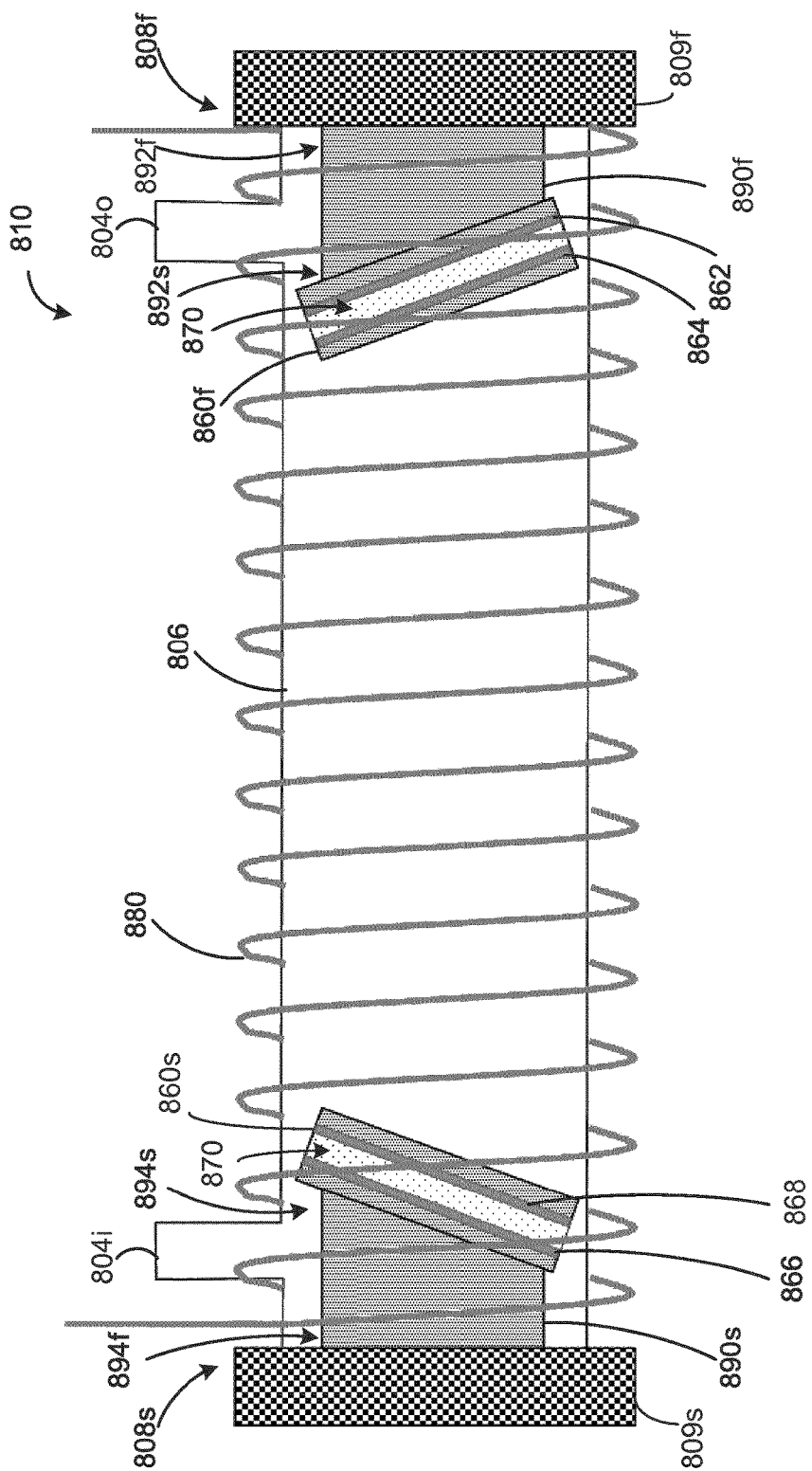

GAS CELL FOR ABSORPTION SPECTROSCOPY

CROSS-REFERENCE TO RELATED PATENT APPLICATIONS

This application claims priority from Chinese Patent Application No. 2015108315786 filed on Nov. 25, 2015 and entitled "Gas Cell For Absorption Spectroscopy", and also claims the benefit of U.S. Provisional Application No. 62/267,709 filed on Dec. 15, 2015 and entitled "Gas Cell For Absorption Spectroscopy". The complete disclosure of each of Chinese Patent Application No. 2015108315786 and U.S. Provisional Application No. 62/267,709 is incorporated herein by reference.

FIELD

The described embodiments relate to a gas cell for absorption spectroscopy.

BACKGROUND

Absorption spectroscopy is often used to analyze a content of various substances. The content analysis may involve identifying components of the substances and/or identifying an amount of a particular component of the substance.

In general, absorption spectroscopy includes spectroscopic techniques that measure an amount of absorption of electromagnetic radiation as a result of the interaction of the electromagnetic radiation with one or more components of the substance. The absorption of the electromagnetic radiation is measured as a function of frequency or wavelength. The component(s) in the substance absorbs a certain amount of energy from the electromagnetic radiation. The intensity of the absorption varies with the component(s) that are present in the substance and as a function of the frequency of the electromagnetic radiation.

SUMMARY

Various embodiments described herein generally relate to a gas cell and system for absorption spectroscopy, and methods for providing a gas cell for absorption spectroscopy.

In accordance with some embodiments, there is provided a method of providing a gas cell for conducting absorption spectroscopy. The method involves: providing a channel having an inlet for receiving a gas sample from a gas source and an outlet for releasing the gas sample from the gas cell; providing a first end component and a second end component for the channel, each of the first end component and the second end component comprising an optically transparent portion, and each of the first end component and the second end component being configured to minimize a temperature difference between a temperature of the respective optically transparent portions and an internal temperature of the channel; mounting the first end component to a first end of the channel, the optically transparent portion of the first end component being positioned for receiving an incident beam from an optical source into the channel; and mounting the second end component to a second end of the channel, the second end being substantially opposite from the first end, the optically transparent portion of the second end component being positioned for permitting optical transmission into and out of the channel.

In some embodiments, the described methods involve: mounting each optically transparent portion to a respective optical frame; and mounting a baffle to the respective optical frame, the baffle shielding the respective optically transparent portion from directly engaging with an external environment of the gas cell.

In some embodiments, the described methods involve: mounting a temperature varying material to each baffle. In some embodiments, mounting the temperature varying material to each baffle can involve surrounding the baffle with a temperature varying coil.

In some embodiments, the described methods involve: positioning each optically transparent portion inwardly within the channel to shield the respective optically transparent portion from directly engaging with an external environment of the gas cell.

In some embodiments, the described methods involve: mounting a first extending member to the channel, the first extending member having a first member end mounted to the first end of the channel and a second member end extending inwardly within the channel, the optically transparent portion of the first end component being mounted at the second member end of the first extending member; and mounting a second extending member to the channel, the second extending member having a first member end mounted to the second end of the channel and a second member end extended inwardly within the channel, the optically transparent portion of the second end component being mounted at the second member end of the second extending member.

In some embodiments, the described methods involve: providing a baffle as each of the first extending member and the second extending member.

In some embodiments, the described methods involve: providing a pair of optical layers as the optically transparent portion of each of the first and second end components. In some embodiments, providing the pair of optical layers as the optically transparent portion of each of the first and second end components involves: substantially vacuum sealing a space between each pair of optical layers.

In some embodiments, the described methods involve: filling a space between each pair of optical layers with an insulation material characterized by a low thermal conductivity. The insulation material may be a gaseous material, such as ambient air.

In some embodiments, the described methods involve: mounting a temperature varying material to the channel. Mounting the temperature varying material to the channel may involve surrounding the channel with a temperature varying coil.

In accordance with some embodiments, there is provided an absorption spectroscopy system including: an optical source for generating an incident beam; a gas cell provided in accordance with a method involving: providing a channel having an inlet for receiving a gas sample from a gas source and an outlet for releasing the gas sample from the gas cell; providing a first end component and a second end component for the channel, each of the first end component and the second end component comprising an optically transparent portion, and each of the first end component and the second end component being configured to minimize a temperature difference between a temperature of the respective optically transparent portions and an internal temperature of the channel; mounting the first end component to a first end of the channel, the optically transparent portion of the first end component being positioned for receiving the incident beam from the optical source into the channel; and mounting the second end component to a second end of the channel, the second end being substantially opposite from the first end, the optically transparent portion of the second end component being positioned for permitting optical transmission into and out of the channel; and a detector positioned relative to the channel for receiving a version of the incident beam and transmitting a data signal corresponding to the version of the incident beam to an absorption spectroscopy analyzer.

In accordance with some embodiments, there is provided a gas cell including: a channel providing at least a passage from an inlet to an outlet, the inlet receiving a gas sample from a gas source and the outlet releasing the gas sample from the gas cell; a first end component mounted to the channel at a first end of the channel, the first end component including a first optically transparent portion positioned inwardly within the channel and positioned to receive an incident beam from an optical source into the channel; and a second end component mounted to the channel at a second end of the channel, the second end being substantially opposite from the first end, and the second end component including a second optically transparent portion positioned inwardly within the channel and positioned to permit optical transmission into and out of the channel.

In some embodiments, the described gas cells include: the first end component comprises a first extending member having a first member end mounted to the first end of the channel and a second member end extending inwardly within the channel, the first optically transparent portion being mounted at the second member end of the first extending member; and the second end component comprises a second extending member having a first member end mounted to the second end of the channel and a second member end extending inwardly within the channel, the second optically transparent portion being mounted to the second member end of the second extending member.

In some embodiments, each of the first extending member and the second extending member includes a baffle.

In some embodiments, at least one of the first optically transparent portion and the second optically transparent portion includes two optical layers.

In some embodiments, a temperature varying material is coupled to the channel.

In some embodiments, the temperature varying material includes a coil wound around the channel.

In some embodiments, at least one surface of each of the first optically transparent portion and the second optically transparent portion is applied with an anti-reflective coating.

In some embodiments, each of the first end component and the second end component is removably mounted to the channel.

In some embodiments, each of the first end component and the second end component is removably mounted to the channel with a threaded coupling.

In accordance with some embodiments, there is provided an absorption spectroscopy system including: an optical source for generating an incident beam; a gas cell having: a channel providing at least a passage from an inlet to an outlet, the inlet receiving a gas sample from a gas source and the outlet releasing the gas sample from the gas cell; a first end component mounted to the channel at a first end of the channel, the first end component including a first optically transparent portion positioned inwardly within the channel and positioned to receive the incident beam from the optical source into the channel; and a second end component mounted to the channel at a second end of the channel, the second end being substantially opposite from the first end, and the second end component including a second optically transparent portion positioned inwardly within the channel and positioned to permit optical transmission into and out of the channel; a detector positioned relative to the channel for receiving a version of the incident beam and transmitting a data signal corresponding to the version of the incident beam to an absorption spectroscopy analyzer.

In accordance with some other embodiments, there is provided a gas cell for absorption spectroscopy. The gas cell includes: a channel providing at least a passage from an inlet to an outlet, the inlet receiving a gas sample from a gas source and the outlet releasing the gas sample from the gas cell; a first end component mounted at a first end of the channel, the first end component comprising a first optical layer and a second optical layer positioned to receive an incident beam from an optical source into the channel; and a second end component mounted at a second end of the channel, the second end being substantially opposite from the first end, and the second end component comprising a first optical layer and a second optical layer positioned to permit optical transmission into and out of the channel.

In some embodiments, the first optical layer of the first end component is substantially parallel with the second optical layer of the first end component; and the first optical layer of the second end component is substantially parallel with the second optical layer of the second end component.

In some embodiments, the first optical layer of the first end component is positioned relative to the second optical layer of the first end component at a first optical layer tilt angle; and the first optical layer of the second end component is positioned relative to the second optical layer of the second end component at a second optical layer tilt angle.

In some embodiments, a value of each of the first optical layer tilt angle and the second optical layer tilt angle varies with at least one of a spacing size between the respective first and second optical layers, a thickness of the respective first optical layer, a thickness of the respective second optical layer, and a diameter of the incident beam In some embodiments, the value of each of the first optical layer tilt angle and the optical layer second tilt angle is greater than 0 degrees and less than or equal to 10 degrees In some embodiments, a space between each of the first optical layers and the respective second optical layers is substantially vacuum sealed.

In some embodiments, a space between each of the first optical layers and the respective second optical layers is filled with an insulation material characterized by a low thermal conductivity. The insulation material may include a gaseous material, such as ambient air.

In some embodiments, at least one surface of each of the first and second optical layers of the respective first and second end components is applied with an anti-reflective coating.

In some embodiments, each of the first and second end components includes: an optical layer frame for containing the respective first and second optical layers, the optical layer frame being mounted to the channel; and a baffle mounted to the optical layer frame.

In some embodiments, a temperature varying material is coupled to each baffle. The temperature varying material can include a coil wound around each baffle.

In accordance with some other embodiments, there is provided an absorption spectroscopy system including: an optical source for generating an incident beam; a gas cell having: a channel providing at least a passage from an inlet to an outlet, the inlet receiving a gas sample from a gas source and the outlet releasing the gas sample from the gas cell; a first end component mounted at a first end of the channel, the first end component comprising a first optical layer and a second optical layer positioned to receive the incident beam from the optical source into the channel; and a second end component mounted at a second end of the channel, the second end being substantially opposite from the first end, and the second end component comprising a first optical layer and a second optical layer positioned to permit optical transmission into and out of the channel; a detector positioned relative to the channel for receiving a version of the incident beam and transmitting a data signal corresponding to the version of the incident beam to an absorption spectroscopy analyzer.

In accordance with some embodiments, there is provided a use of any one of the gas cells described herein conducting an absorption spectroscopy measurement of a gas sample.

BRIEF DESCRIPTION OF THE DRAWINGS

Several embodiments will now be described in detail with reference to the drawings, in which:

FIG. 2A is a cross-sectional view of an example gas cell in accordance with an example embodiment;

FIG. 2B shows the example gas cell in FIG. 2A in accordance with another example embodiment;

FIG. 3 is a cross-sectional view of another example gas cell in accordance with an example embodiment;

FIG. 7A is a cross-sectional view of yet another example gas cell in accordance with an example embodiment;

FIG. 7B shows the example gas cell in FIG. 7A in accordance with another example embodiment;

FIG. 8 is a cross-sectional view of another example gas cell in accordance with an example embodiment.

Figure 1A:
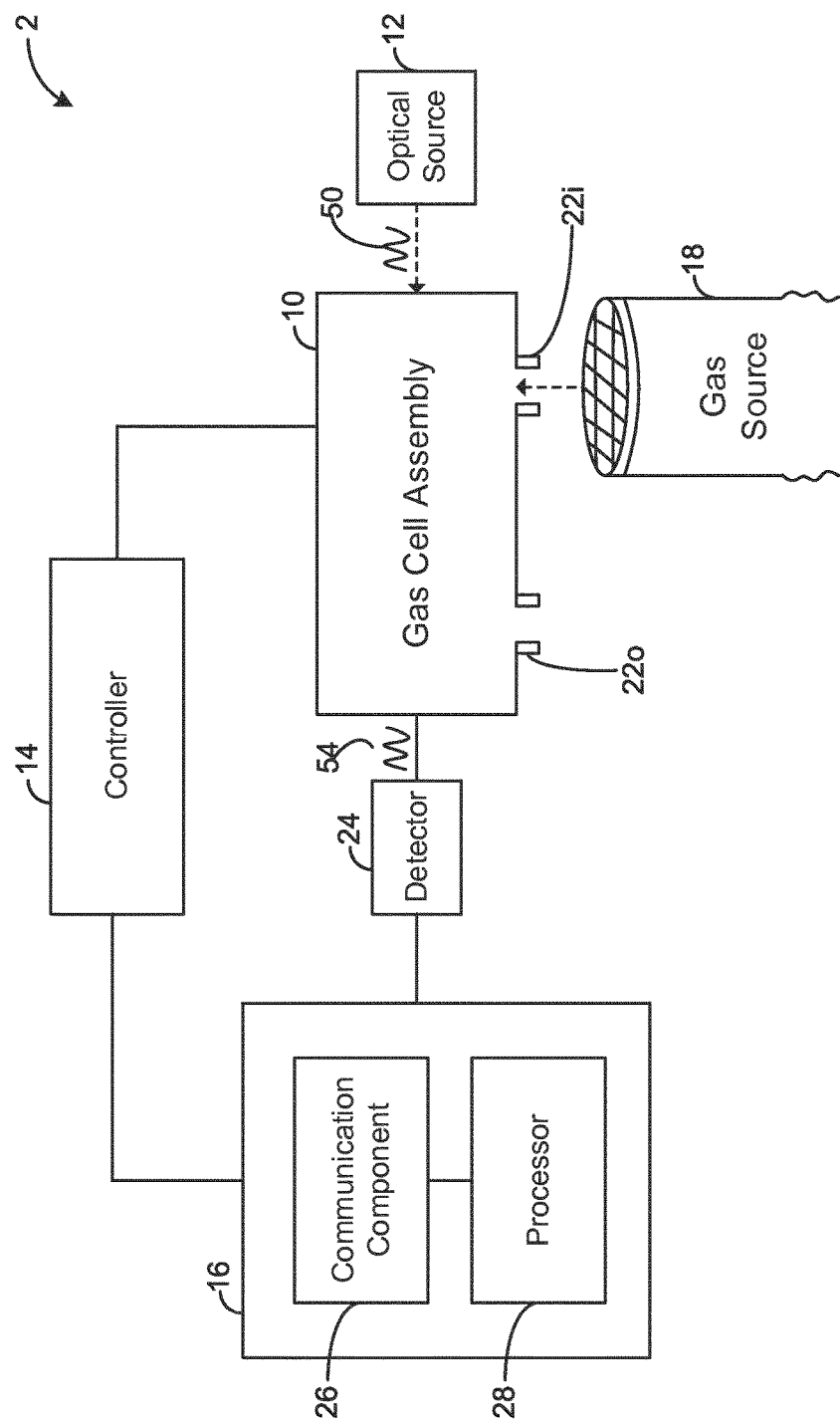
FIG. 1A is a block diagram of components interacting with a gas cell assembly in accordance with an example embodiment.

The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps.

DESCRIPTION OF EXAMPLE EMBODIMENTS

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that the term "coupled" used herein indicates that two elements can be directly coupled to one another or coupled to one another through one or more intermediate elements.

Optical absorption spectroscopy involves directing an optical beam from an optical source through a substance, such as a gas. The substance may be in an enclosed environment or an open path. The intensity of the absorption varies with, at least, the different components of the substance. After transmitting through the substance, the transmitted optical beam is received by a detector. The detector can then provide a data signal related to the transmitted optical beam to an analyzer device for conducting the absorption spectroscopy analysis.

The absorption of the electromagnetic radiation at a specific frequency by the substance can generally be quantified by the Beer-Lambert law:

$$I = I_0 e^{-kcL}$$

where "I" represents an intensity of the detected optical beam, "$I_0$" represents an intensity of the initial optical beam provided by the optical source, "k" represents an absorptivity of an attenuator in the substance at a given temperature and frequency, "c" represents a concentration of the attenuator in the substance and "L" represents a path length of the optical beam through the substance. According to the Beer-Lambert law, the intensity of the detected optical beam (I) is generally inversely proportional to the path length (L). The inverse relationship between the detected intensity and the path length can be particularly evident for components within the substance that are present at very low levels and/or particularly weak absorbers. The inverse relationship between the detected intensity and the path length is illustrative of the increased absorption by the component(s) of the substance when an increased path length is provided. Since increasing the path length can increase the absorption by the component(s) of the substance, the sensitivity of the absorption spectroscopy analysis can therefore be increased.

The sensitivity of the content analysis in absorption spectroscopy can be critical for certain industries. Coal-burning power plants, for example, are becoming more regulated by the relevant regulatory bodies in terms of mono-nitrogen oxides ($NO_x$) emissions. The ability to accurately identify the components of the substances so that appropriate feedback can be sent by the relevant control systems can therefore be critical.

The absorption of electromagnetic radiation by the components of the substance can either be made in-situ or extractive. In-situ analysis involves passing electromagnetic radiation through the substance at the location where the substance is formed. Extractive analysis involves passing electromagnetic radiation through the substance after the substance is extracted from its original location and brought into a measurement environment, such as a closed container. Typically, extractive absorption spectroscopy measurements are performed using an absorption cell, or a gas cell, of a suitable length. A length of the gas cell can be restricted due to practical limitations, such as portability of the gas cell and/or space availability at the measurement site. The substance being tested can be referred to as a gas sample.

Multi-pass gas cells accommodate an increased path length. The use of multi-pass gas cells can improve absorption detection sensitivity without significantly increasing the size of the measurement instrument. Typically, multi-pass gas cells include a set of mirrors that is exposed to the gas sample. The set of mirrors reflects the optical beam multiple times so that the overall path length through the substance increases substantially without needing to increase the length of the gas cell itself.

Different multi-pass gas cells have been developed for increasing the path length. Common types of multi-pass cells can include gas cells based on the Herriott and White gas cell designs.

The Herriott gas cell includes two mirrors with identical focal length and the two mirrors are separated from each other by a distance, "D". The mirrors can have various forms, such as spherical, astigmatic or other complex forms. The mirrors within the Herriott gas cell are usually enclosed in a suitable container with inlet and outlet connections to allow the sample gas to flow through the gas cell at the required rate. The container used in the Herriott gas cell is usually configured to allow entry and exit of optical beams.

The White gas cell includes three spherical and concave mirrors with the same radius of curvature. Two neighbouring mirrors can be provided across from the third mirror. One of the neighbouring mirrors can be configured for receiving at least an incident beam from the optical source, and the other neighbouring mirror can be configured for, at least, directing the last reflected beam towards the detector. During the transit of the versions of the incident beam within the White gas cell, the neighbouring mirrors can alternately reflect the versions of the incident beam received from the third mirror. Similar to the Herriott gas cell, the mirrors in the White gas cell are also typically enclosed in a suitable container with inlet and outlet connections to allow the sample gas to flow through the gas cell.

During operation of the gas cell and in particular industrial settings, even if the gas is filtered, dust and/or other contaminants are often drawn into the gas cell. Over time, the dust and contaminants become deposited on the mirrors, and depending on the type of contaminant, the contaminants may even react with the surfaces of the mirror. As a result, the reflectivity of the mirrors can degrade over time. It is possible that the deterioration of the mirrors can be compensated with software but the deterioration of the mirrors will nevertheless cause a reduction in the sensitivity of the detected intensity of the optical beam.

The mirrors in the Herriott gas cell and the White gas cell are in direct contact with the gas sample and are, therefore, subject to any dust and/or contaminants that may be in the gas sample. Depending on the environment, the gas sample may include corrosive contents that can cause corrosion in the components of the gas cell, such as the mirrors. The degradation of the reflectivity of the mirrors over time can, therefore, significantly reduce any benefits that may result from the use of the multi-pass cell. Cleaning or replacing the mirrors can be cumbersome since the mirrors need to be carefully aligned.

The gas cell may be required to be operated at a temperature that is well above ambient. For instance, higher temperatures may be required to prevent condensation from being formed in the gas cell since condensation can obscure the optical beam. Certain undesired chemicals tend to react at lower temperatures and affect the composition of the substance. The undesired chemicals may also react to form contaminants that can degrade the components of the measurement instrument. For example, in coal-burning power plants, ammonia is often injected into the resulting flue gas to reduce $NO_x$ emissions. However, over-injection of the ammonia may result in ammonia slip, or excess ammonia, within the flue gas. Depending on the temperature of the flue gas, the excess ammonia and the sulfur compounds formed during the combustion of coal can react to form ammonium bisulfate (ABS). ABS formation can clog filters and cloud the surfaces of mirrors and windows of the gas cell. ABS may form even at temperatures of up to 260° C., for example.

Unfortunately, there can be challenges to operating the gas cell at high temperatures. For example, the high temperature that may be required to operate the gas cell can affect the alignment of the optical components. Temperature changes can affect alignment and therefore, optical alignment needs to be performed when the gas cell has reached the temperature at which it will operate.

Direct heating of the windows of the gas cell can minimize some of the challenges related to the alignment of the optical components. However, direct heating typically requires heating elements to be attached to the windows, which can reduce the transparent area of the windows and thus, limit the variety of optical beams that can be used for gas measurements. Window sealing elements, such as o-rings and gaskets, that can facilitate continuous operation at elevated temperatures (e.g., higher than 300° C.) can be very expensive and may even be difficult to obtain.

Reference is first made to FIG. 1A, which is a block diagram 2 of components interacting with an example gas cell assembly 10. The gas cell assembly 10 has, at least, an inlet 22$i$ and an outlet 22$o$. The inlet 22$i$ and outlet 22$o$ may be closed to contain a gas sample within the gas cell assembly 10. As shown, the gas cell assembly 10 can receive an incident beam 50 generated by an optical source 12. The incident beam 50 is transmitted within the gas cell assembly 10 and a version of the incident beam 50, or a transmitted beam 54, is received by a detector 24.

As will be described with reference to FIGS. 1B, 2A, 2B, 3, 4A to 4B, 7A to 7C and 8, the gas cell assembly 10 includes a gas cell that can receive and contain the gas sample. The embodiments of the gas cell described herein include, at least, a channel in which the gas sample is received at the inlet 22$i$ and is released from the outlet 22$o$.

Figure 1B:
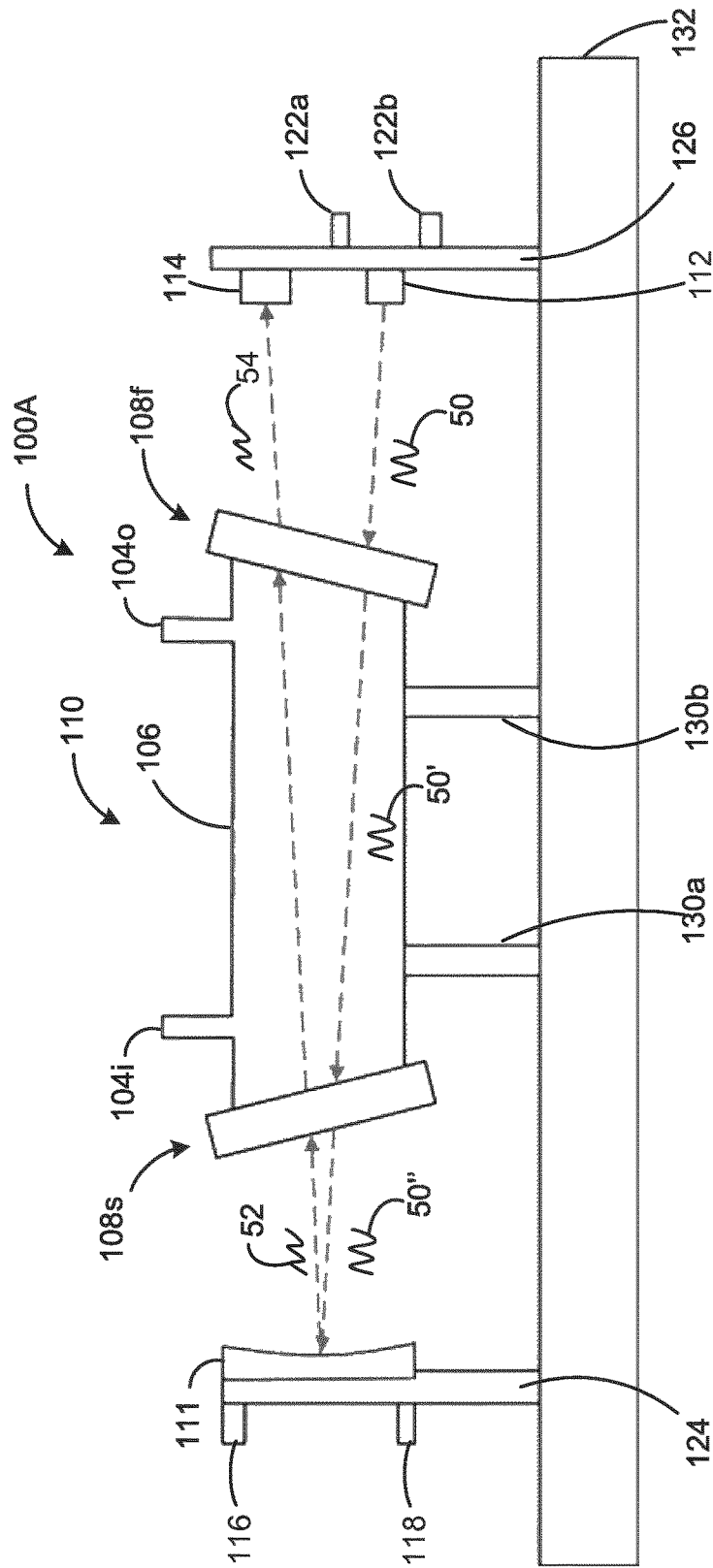
FIG. 1B is a cross-sectional view of an example gas cell assembly in accordance with an example embodiment.

For example, as shown in FIGS. 1A and 1B, the inlet 22*i* of the gas cell assembly 10 is coupled to a gas source 18 to receive the gas sample. Each end of the channel is mounted with an end component 108. At each end of the channel, there is an optically transparent portion to permit optical transmission into and out of the channel.

FIG. 1B shows a cross-sectional view of an example gas cell assembly 100A. When the incident beam 50 is received at a first end component 108*f* mounted to a first end of the channel, a version of the incident beam 50 is transmitted towards a second end component 108*s* mounted to a second end of the channel while interacting with the gas sample inside the channel 106. Each of the first end component 108*f* and second end component 108*s* in this embodiment includes an optically transparent portion that can permit the transmission of optical beams, such as beams 50, 52 and 54 shown in FIG. 1B, into and out of the channel 106.

As shown in FIG. 1B, a version of the incident beam 50, or a first transmitted beam 50', enters the channel 106 instead of the original incident beam 50 due to possible reflection losses at the first end component 108*f*. At the second end component 108*s*, another version of the incident beam 50', or a second transmitted beam 50", is directed towards the reflective surface 111. An intensity of the second transmitted incident beam 50" is reduced due to absorption by the gas sample while inside the channel 106 and possible reflection losses at the second end component 108*s*.

The reflective surface 111 is positioned outside the gas cell 110, and positioned relative to the second end component 108*s* to receive the second transmitted beam 50" from the second end component 108*s* and to direct a reflected beam 52 towards the second end component 108*s*.

The reflected beam 52 then travels through the second end component 108*s* into the channel 106 and towards the first end component 108*f*. The first end component 108*f* then transmits a version of the reflected beam 52, or a last reflected beam 54, towards the detector 114. As can be seen in FIG. 1B, only the interior surfaces of the optically transparent portions of each of the first end component 108*f* and the second end component 108*s* are exposed to the gas sample.

To increase the path length, the optical beams can enter and exit the channel 106 via a different section on the optically transparent portion of the second end component 108*s*. The section on the second end component 108*s* at which the reflected beam 52 enters can vary with, at least, an angle of incidence of the second transmitted beam 50" and a curvature of the reflective surface 111. The reflective surface 111 may be a mirror, such as a concave mirror.

From the example transmission path shown in FIG. 1B, it can be seen that the path length of the incident beam 50 can be extended without increasing the length of the channel 106. In the example shown in FIG. 1B, the path length of the incident beam 50 has increased by at least two times and as a result, the sensitivity of the absorption measurement has also increased.

The detector 114, as shown in FIG. 1B, is positioned relative to the channel 106 for receiving a version of the incident beam 50 (i.e., a last reflected beam 54) after the incident beam 50 has passed through the channel 106 multiple times. The detector 114 can, in some embodiments, transmit a data signal corresponding to the received version of the incident beam 50 to an absorption spectroscopy analyzer for conducting the absorption spectroscopy measurement. The data associated with the received beam may include optical data. The gas cell assembly 10 can also be in electronic communication with a controller 14 for receiving control signals associated with the operation of the gas cell assembly 10.

When the detector 114 receives the data signal in the form of an optical signal, the detector 114 can convert the optical signal to an electrical signal. For example, the detector 114 can determine a current value that is proportional to the intensity of the last reflected beam 54 received by the detector 114. The detector 114 may, in some embodiments, include multiple detector components for receiving different data signals. For example, the detector 114 may include a first detector component for determining an intensity of a first optical beam and a second detector component for determining an intensity of a second optical beam that is different from the first optical beam. The various detector components may be arranged together in one unit or provided as physically separate units.

Referring again to FIG. 1A, the detector 24 may transmit an electrical signal to the computing device 16 via a connector, such as a coaxial cable. In some embodiments, the detector 24 may further convert the electrical signal to another form, such as an optical signal representing the electrical signal using an electrical to optical signal converter. The resulting optical signal can be transmitted to the computing device 16 via fiber optic cables.

The computing device 16 can receive data signals from the detector 24 for conducting the relevant analysis on the information provided by the data signals. For example, the computing device 16 may include or may be an absorption spectroscopy analyzer for conducting an absorption spectroscopy analysis on the information provided by the data signals. The computing device 16 may include an electronic tablet device, a personal computer, workstation, server, portable computer, mobile device, personal digital assistant, laptop, smart phone, portable electronic devices, measurement instrument, or any combination of these.

The optical source 12 may also be provided as part of the computing device 16. For example, the incident beam 50 generated by the optical source 12 can be transmitted from the computing device 16 via a fiber-optic cable when the optical source 12 is separately located from the gas cell assembly 10.

The computing device 16 can include, at least, a communication component 26 and a processor 28. It should be noted that, in some embodiments, the communication component 26 and the processor 28 may be combined or may be separated into one or more further components. The communication component 26 and the processor 28 may be implemented using software, hardware, or a combination of software and hardware.

The communication component 26 is operable to receive the data signals from the detector 24. The communication component 26 may include at least one of a serial port, a parallel port or a USB port. The communication component 26 may also include at least one of an Internet, Local Area Network (LAN), Ethernet, Firewire, modem, or other wireless connections. Various combinations of these elements may be incorporated within the communication component 26.

The processor 28 can conduct the analysis based on the data signals received by the communication component 26, or may, in some embodiments, cause the relevant analysis to be conducted by one or more other components (not shown). The processor 28 may be any suitable controllers or digital signal processors that can provide sufficient processing power depending on the configuration, purposes and requirements of the computing device 16. In some embodiments, the processor 28 can include more than one processor with each processor being configured to perform different dedicated tasks.

In some embodiments, the computing device 16 may also include a memory (not shown). The memory can include RAM, ROM, one or more hard drives, one or more flash drives or some other suitable data storage element such as disk drives, etc. The memory may be internal to the computing device 16 or separate from the computing device 16 but in electronic communication with the computing device 16.

The optical source 12 is positioned relative to the gas cell assembly 10 for transmitting the incident beam 50 towards the gas cell containing the gas sample. For example, FIG. 1B shows the optical source 112 positioned relative to the gas cell assembly 100A for transmitting the incident beam 50 towards the gas cell 110. A wavelength of the incident beam 50 can vary with various aspects of the absorption spectroscopy analysis to be conducted, such as the type of the absorption spectroscopy analysis, the gas sample to be analyzed, and/or the content intended to be identified. For example, near or mid-infrared beams can be used for measuring various different types of gases, such as very low levels of ammonia gas. For certain other gases, visible and/or ultra-violet (UV) beams may also be used. The incident beam 50 may, in some embodiments, be a collimated beam.

The optical source 12 may include an optic generator for generating the incident beam 50 or may include launching optics that receives the incident beam 50 from a remote optic generator via fiber-optic cables.

For example, when the optical source 12 includes launching optics, the optic generator may be provided at the computing device 16. In some embodiments, the optic generator may include a tunable diode laser that is located at the computing device 16, which may be an optical spectroscopy analyzer. The incident beam 50 may therefore be a laser beam that is provided from the tunable diode laser to the optical source 12 via a fiber-optic cable that can support the wavelength of the laser beam.

Similar to the detector 24, the optical source 12 may include multiple optical source components to transmit different incident beams 50. For example, the optical source 12 may include a first optical source component for transmitting a first incident beam and a second optical source component for transmitting a second incident beam. The various optical source components may be arranged together in one unit or provided as physically separate units. As will be described, the gas cell assembly 10 may receive multiple different incident beams 50 for identifying different gas components within the gas sample and/or measuring an amount of each of the different gas components within the gas sample.

The gas source 18 can vary with the test environment. For example, in power generation plants, the gas source 18 may be a vent opening of a pipeline or a duct. In laboratory test environments, the gas source 18 may be an experimental gas formed from a reaction. In chemical plants, the gas source 18 may be a process gas. In combustion applications, the gas source 18 may be an off-gas such as carbon monoxide and/or carbon dioxide. In incinerators, the gas source 18 may be a stack where, for example, hydrogen chloride needs to be measured.

The controller 14 can be in electronic communication with the computing device 16 and the gas cell assembly 10. The computing device 16 can generate control signals for the controller 14 based on the analysis of the data signals. The control signals can indicate to the controller 14 that the operation of the gas cell assembly 10 should be adjusted and/or how the operation of the gas cell assembly 10 should be adjusted.

In some embodiments, one or more of the gas cell assembly 10, the computing device 16 and the controller 14 may be configured to communicate via a network (not shown) capable of carrying data. An example network may be the Internet, Ethernet, coaxial cable, fiber optics, satellite, mobile, wireless fixed line, local area network, wide area network, and others, including any combination of these, capable of interfacing with, and enabling communication between the various components.

Referring again to FIG. 1B, the gas cell assembly 100A includes a gas cell 110, and the reflective surface 111. The optical source 112 and the detector 114 are positioned relative to the gas cell assembly 100A. Each of the gas cell 110, the reflective surface 111, the optical source 112 and the detector 114 can be mounted to a base 132. In the example embodiment shown in FIG. 1B, the gas cell 110 is mounted to the base 132 with mounts 130a and 130b, the reflective surface 111 is mounted to the base 132 with a mount 124, and the optical source 112 and the detector 114 are mounted to the base 132 with another mount 126.

Alignment controls can be operably coupled to each of the mounts 124 and 126 to adjust the orientation of the components mounted thereon. As illustrated in FIG. 1B, alignment controls 116 and 118 are operably coupled to the mount 124 for adjusting the alignment of the reflective surface 111 with respect to the gas cell 110 and/or the optical source 112, and alignment controls 122a and 122b are operably coupled to the mount 126 for adjusting the alignment of the optical source 112 with respect to the first end component 108f and the reflective surface 111. The alignment controls 116, 118, 122a and 122b may be a screw and/or other similar components that can be operated for adjusting an orientation of another component.

Figure 1C:
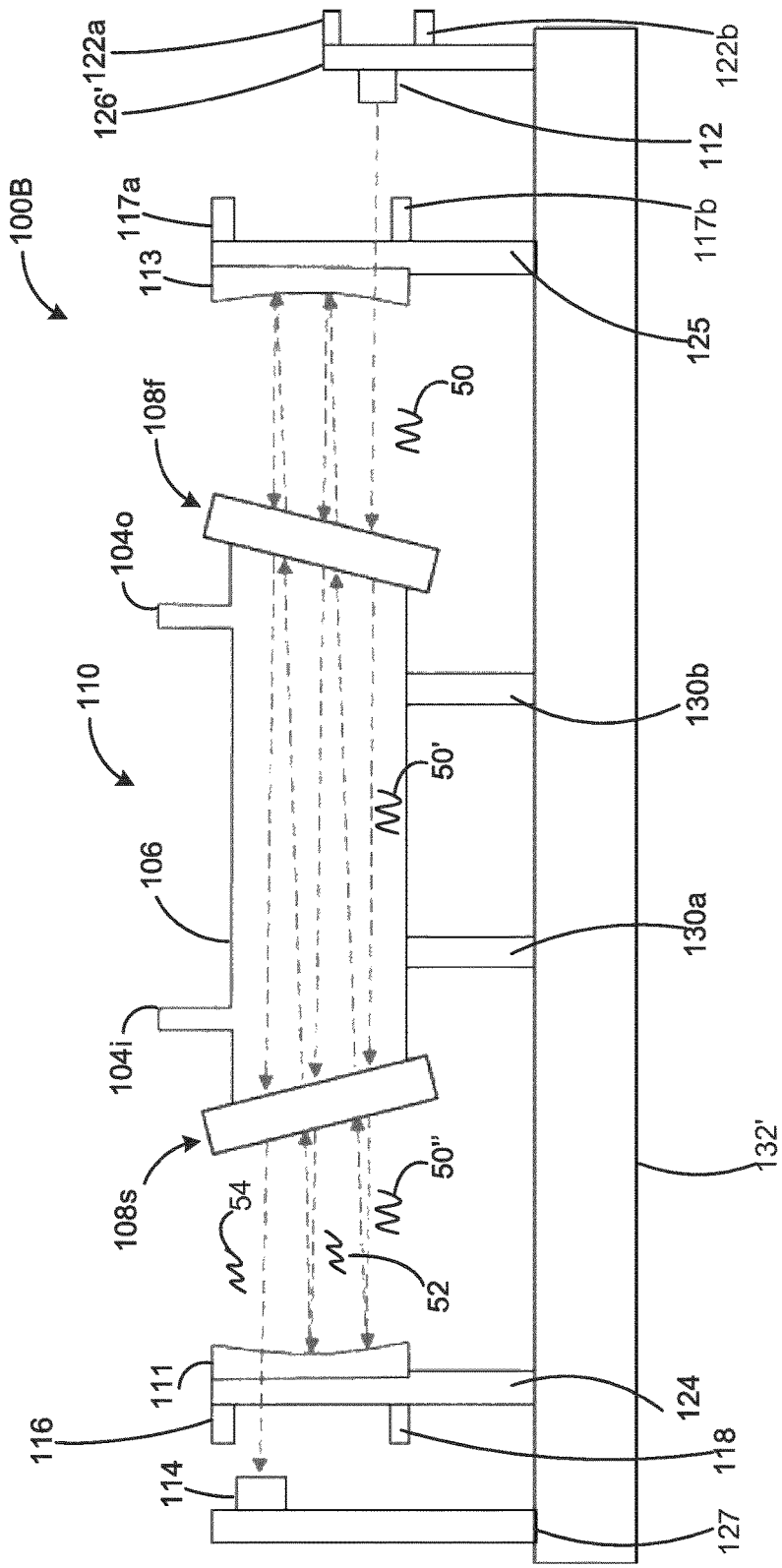
FIG. 1C is a cross-sectional view of another example gas cell assembly in accordance with an example embodiment.

The various embodiments of the gas cell 110 described herein with reference to FIGS. 2A, 2B, 3, 4A, 4B, 7A to 7C and 8 may be used in other configurations of the gas cell assembly 100A. For example, another embodiment of a gas cell assembly 100B is shown in FIG. 1C.

The gas cell assembly 100B can include a second reflective surface 113 positioned across from the first end component 108f and the detector 114 can then be positioned at an opposite end of the channel 106 from the optical source 112. As shown in FIG. 1C, the detector 114 can be mounted across from the second end component 108s and behind the first reflective surface 111 with a mount 127. The second reflective surface 113 can be mounted with mount 125 across from the first end component 108f. Alignment controls 117a and 117b can be operably coupled to the mount 125 for adjusting the alignment of the second reflective surface 113. The optical transmission path includes multiple reflections between the first reflective surface 111 and the second reflective surface 113, as shown in FIG. 1C.

The gas cell 110 includes the channel 106, which provides a passage from a first end to a second end, and also includes an inlet 104i and an outlet 104o. The inlet 104i can receive a gas sample from the gas source 18 and the outlet 104o can release the gas sample from the gas cell 110. Each of the first and second end components 108f and 108s shown in FIG. 1B includes an optically transparent portion. Various embodiments of the first and second end components will be described with reference to FIGS. 2A, 2B, 3, 4A, 4B, 7A to 7C and 8.

Referring still to FIG. 1B, at the first end of the channel 106, a first end component 108f is mounted thereon. The first end component 108f includes an optically transparent portion that can receive the incident beam 50 generated by the optical source 112 into the channel 106. At the second end of the channel 106 that is substantially opposite from the first end of the channel 106, a second end component 108s is mounted thereon. Similar to the first end component 108f, the second end component 108s includes an optically transparent portion that permits optical transmission into and out of the channel 106. For example, as shown in FIG. 1B, the second end component 108s can receive the reflected beam 52 from the reflective surface 111, and the first end component 108f can transmit the last reflected beam 54 towards the detector 114.

The first and second end components 108f and 108s can be securably and removably mounted to the channel 106. The secured coupling may include a seal, such as o-rings, a threaded coupling, and/or other similar types of couplings.

Example embodiments of the gas cell 110 will now be described with reference to FIGS. 2A, 2B, 3, 4A, 4B, 7A to 7C and 8.

The temperature of the components of the gas cell 110 may be regulated to facilitate the operation of the gas cell 110. In particular, the temperature of the channel 106 can be regulated to prevent formation of condensation at the optically transparent portions and formation of undesired chemicals that may then obstruct the optically transparent portions. In coal-burning power plants, for example, the increased temperature of the channel 106 can reduce the formation of ammonium bisulfate (ABS). Also, as will be described with the various embodiments of the gas cell 110 shown in FIGS. 2A, 2B, 3, 4A, 4B, 7A to 7C and 8, the temperature difference between the surfaces of the optically transparent portions of the gas cell 110 and inside the channel 106 can also be minimized. By minimizing the temperature difference between a temperature of the optically transparent portions and an internal temperature of the channel 106, the likelihood of condensation and ABS deposits forming on the interior surfaces of the first and second end components 108f and 108s can be significantly reduced.

Reference will now be made to FIG. 2A, which is a cross-sectional view of an example gas cell 210A.

The gas cell 210A includes a channel 206 with an inlet 204i for receiving the gas sample and an outlet 204o from which the gas sample can be released.

To control the temperature inside the channel 206, a temperature varying material can be coupled to the channel 206. In the example shown in FIG. 2A, a temperature varying coil 280 is wound around the channel 206. The temperature varying material may be a heating material or a cooling material. The type of material that is used to form the channel 206 can also affect the amount of temperature change that can be provided by the temperature varying coil 280. In some embodiments, an insulation material (not shown in FIG. 2A) may be enclosed around the temperature varying coil 280 to further stabilize the temperature at the channel 206.

When the temperature varying material acts as a heating material, the heating material can cause a temperature of the channel 206 to increase and, as a result, the temperature of the gas sample within the channel 206 to also increase. When the temperature varying material acts as a cooling material, the cooling material can cause a temperature of the channel 206 to decrease and as a result, the temperature of the gas sample within the channel 206 to also decrease. The temperature of the channel 206 may be increased to exceed a temperature of the external environment of the gas cell 210A or decreased to fall below the temperature of the external environment.

Each end of the channel 206 is enclosed by end components 208. A first end component 208f is mounted at a first end of the channel 206 and a second end component 208s is mounted at a second end of the channel 206. Each of the first and second end components 208f and 208s includes an optically transparent portion 262, 266, respectively. The optically transparent portions 262 and 266 can be contained in a respective optical frame 260f, 260s.

Also, as shown in FIG. 2A, a first and second baffle 290f, 290s is mounted to the respective optical frames 260f and 260s to form the respective end components 208f, 208s. Each of the baffles 290f, 290s may be mounted coaxially with an axis along a length of the channel 206.

The baffles 290f, 290s can help to stabilize the temperature between the channel 206 and the optically transparent portions 262 and 266 by shielding the optically transparent portions 262 and 266 from directly engaging with the external environment of the gas cell 210A, such as the test environment. The first baffle 290f can be mounted to the optical frame 260f so that the first optically transparent portion 262 is not directly exposed to the test environment. Similarly, the second baffle 290s can be mounted to the optical frame 260s to protect the second optically transparent portion 266 from being directly exposed to the test environment. The temperature of the optically transparent portions 262 and 266 can, therefore, be regulated, to an extent with the baffles 290f, 290s.

During the optical transmission within a gas cell assembly with the gas cell 210A, residual reflection is likely to result from the interaction of the optical beam with the optically transparent portions 262 and 266 since the optically transparent portions 262 and 266 can act as relatively weak reflective surfaces. Anti-reflective material that is applied to the surface of the optically transparent portions 262 and 266 can, to an extent, minimize the residual reflection. However, some residual reflection may nevertheless result from the interaction of the optical beam with the optically transparent portions 262 and 266.

To minimize the optical noise (etalons) that may be caused by the residual reflection, the second optically transparent portion 266 can be tilted towards the reflective surface 111 and the first optically transparent portion 262 can also be tilted towards the optical source 112. In some embodiments, the tilt of the second optically transparent portion 266 with respect to the reflective surface 111 and the tilt of the first optically transparent portion 262 with respect to the optical source can be mirror symmetry to each other.

As shown in FIG. 2A, an axis 209s along a length of the second optically transparent portion 266 can be oriented at an end portion tilt angle 294s ($\theta_{t,s}$) relative to an axis 207 orthogonal to a length of the channel 206. Similarly, an axis 209f along a length of the first optically transparent portion 262 can be oriented at an end portion tilt angle 294f ($\theta_{t,f}$) relative to the axis 207.

The end portion tilt angle 294s can be substantially equal in value to the end portion tilt angle 294f so that the optical beam does not deviate from the transmission path. In this embodiment, the tilt angles 294s, 294f have mirror symmetry to each other. For example, when the incident beam 50 is received at the first optically transparent portion 262 from the optical source 112 and deviated (e.g., shifted) from the optical transmission path by the end portion tilt angle 294f, the optical beam transmitted by the channel 206 thereafter and received at the second optically transparent portion 266 can be realigned to the optical transmission path by the second optically transparent portion 266, which is tilted at the end portion tilt angle 294s. The mirror symmetry of the end portion tilt angles 294f and 294s can compensate for each other.

FIG. 2B shows another example gas cell 210B.

Similar to gas cell 210A shown in FIG. 2A, the first and second end components 208f and 208s' of the gas cell 210B includes baffles 290f, 290s mounted to the respective optical frames 260f, 260s. Unlike the gas cell 210A, the gas cell 210B includes a temperature varying material coupled to each of the baffles 290f, 290s. Similar to the temperature varying coil 280, the temperature varying material coupled to the baffles 290 is a temperature varying coil 282 wound around each baffle 290f, 290s. The temperature varying coil 282 can help to stabilize the temperature at optically transparent portions 262 and 266 to minimize the temperature gradient between the optically transparent portions 262 and 266 and the interior of the channel 206.

The temperature varying coils 280, 282 can be controlled to effect a generally uniform temperature at the optically transparent portions 262 and 266, and the interior of the channel 206. For example, the temperature varying coils 280 and 282 can be controlled to provide the same temperature to the respective components of the gas cell 210B. In some other embodiments, depending on the temperature measured at each of the optically transparent portions 262 and 266, and the channel 206, the temperature of each of the temperature varying coils 280 and 282 may be controlled to provide different temperatures at the respective components of the gas cell 210B in order to provide an overall uniform temperature at the gas cell 210B.

FIG. 3 is a cross-sectional view of another example gas cell 310.

Like the gas cells 210A, 210B, the gas cell 310 also includes a channel 306 with an inlet 304i for receiving the gas sample and an outlet 304o from which the gas sample can be released. A temperature varying material, namely a temperature varying coil 380, is coupled to the channel 306 to control the temperature inside the channel 306. Like the temperature varying coil 280, temperature varying coil 380 may be a heating material or a cooling material.

The channel 306 is enclosed by a first end component 308f at a first end and a second end component 308s at a second end. The first and second end components 308f, 308s are securably and removably mounted to the respective ends of the channel 306 with a coupling 309f, 309s. The coupling 309f, 309s may be a threaded coupling or other similar type of couplings.

Unlike the optically transparent portions 262, 266 of the gas cells 210A, 210B, the optically transparent portions 362, 366 of the gas cell 310 are coupled to the first and second ends, respectively so as to be positioned inwardly within the channel 306. The position of the optically transparent portions 362, 366 within the length of the channel 306 can vary with the overall length of the channel 306 and the desired path length for the overall optical transmission. Depending on the type of absorption spectroscopy to be conducted, a shorter path length may be sufficient for obtaining data at a desired level of sensitivity and so, the optically transparent portions 362, 366 can be mounted further within the channel 306 in order to enhance the temperature stability of the optically transparent portions 362, 366. In some absorption spectroscopy analysis, a high level of sensitivity for the data may be required and so, a longer path length will be desired.

The optically transparent portions 362, 366 can be mounted closer to either ends of the channel 306 in order to maximize the path length.

By positioning the optically transparent portions 362, 366 inwardly within the channel 306, the optically transparent portions 362, 366 can be shielded from being directly engaged with the external environment of the gas cell 310. The temperature of the optically transparent portions 362, 366 can also benefit from being regulated by the internal temperature of the channel 306 and/or the temperature varying coil 380 surrounding the channel 306.

To position the optically transparent portions 362, 366 inwardly with the channel 306, an extending member can be mounted to one end of the channel 306, such as via the coupling 309f, 309s, while extending inwardly within the channel 306. As shown in FIG. 3, a first extending member 390f has a first member end 392f that is mounted to the first end of the channel 306 via the coupling 309f. The first extending member 390f has a second member end 392s that extends inwardly within the channel 306. The first optically transparent portion 362 is mounted to the first extending member at the second member end 392s.

In the example shown in FIG. 3, a first optical frame 360f contains the first optically transparent portion 362 and the first optical frame 360f is mounted to the second member end 392s. In some other embodiments, the first optically transparent portion 362 can be mounted directly to the first extending member 390f without the first optical frame 360f.

A second extending member 390s with a first member end 394f and a second member end 394s similarly mounts the second optically transparent portion 366 to the channel 306. A second optical frame 360s contains the second optically transparent portion 366 and the second optical frame 360s is mounted to the second extending member 390s at the second member end 394s.

Baffles may be used as the extending members 390f, 390s, in some embodiments.

In some embodiments, the first and second end components 108f and 108s can each include at least two optical layers. Such example embodiments will be described with reference to FIGS. 4A, 4B, 7A to 7C and 8.

Figure 4A:
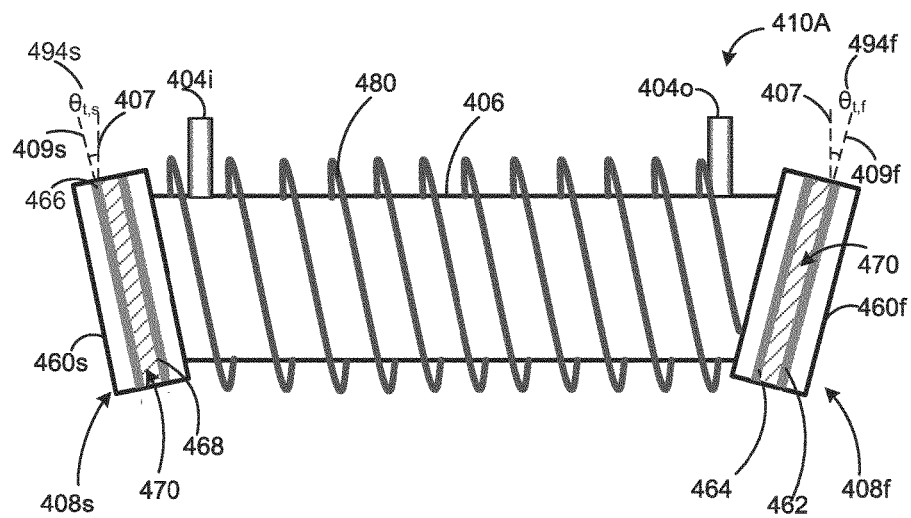
FIG. 4A is a cross-sectional view of an example gas cell in accordance with an example embodiment.

FIG. 4A is a cross-sectional view of an example gas cell 410A.

Similar to the gas cell 210A shown in FIG. 2A, the gas cell 410A includes a channel 406 with an inlet 404i and an outlet 404o. The channel 406 is also wound with a temperature varying coil 480 to help regulate the temperature of the gas cell 410A and in particular, the temperature of the channel 406. The channel 406 is enclosed by a first end component 408f mounted at a first end of the channel 406 and a second end component 408s mounted at a second end of the channel 406. Each of the first and second end components 408f and 408s includes a respective optical frame 460f, 460s for containing a pair of optical layers.

As shown in FIG. 4A, the first end component 408f includes a first optical layer 462 that is spaced from a second optical layer 464, and the second end component 408s includes a first optical layer 466 that is spaced from a second optical layer 468. The first and second optical layers 462, 464 of the first end component 408f are positioned to receive the incident beam 50 from the optical source 112, and the first and second optical layers 466, 468 of the second end component 408s are positioned to permit optical transmission into and out of the channel 406.

The first and second optical layers 462, 464 are contained in the first optical frame 460f, and the first and second optical layers 466, 468 are contained in the second optical frame 460s. For example, the first optical frame 460f can include grooves for receiving each of the first and second optical layers 462 and 464, and the second optical frame 460s can include grooves for receiving each of the first and second optical layers 466 and 468. The first and second optical frames 460f, 460s are mounted to the channel 406.

In FIG. 4A, the optical layer pairs 462, 464 and 466, 468 are generally parallel to each other. In some embodiments, such as the gas cell 410B shown in FIG. 4B, the first optical layers 462, 466 and the second optical layers 464, 468 can be oriented at different angles with respect to each other. The optical frames 460f, 460s can accommodate the orientation of the first optical layers 462, 466 with respect to the second optical layer 464, 468.

The space 470 between each of the first optical layers 462, 466 and the respective second optical layers 464, 468 can help to stabilize the internal temperature of the gas cell 410A. This can be particularly important during operation of the gas cell 410A at high temperature.

In some embodiments, the space 470 between each pair of optical layers, namely first and second optical layers 462 and 464, and first and second optical layers 466 and 468, can be evacuated to form a reduced pressure section. The space 470, as a result, can be nearly vacuum sealed. In some embodiments, the space 470 between the first and second optical layers 462 and 464, and the space 470 between the first and second optical layers 466 and 468 can be sealed when filled with an insulation material characterized by a low thermal conductivity. The insulation material can be a gaseous material, such as ambient air.

The insulation material can insulate the interior of the channel 406 from the test environment so the temperature inside the channel 406 can be isolated from the temperature of the test environment. Heat, for example, can be trapped between each pair of optical layers, such as first and second optical layers 462 and 464, and first and second optical layers 466 and 468, so that the temperature of the optical layers that are in direct contact with the gas sample (e.g., the second optical layers 464, 468) can be relatively stable.

The pair of optical layers at the first and second end components 408f and 408s can minimize at least some of the challenges associated with operating gas cells, such as 410A, at high temperatures for conducting absorption spectroscopy analysis.

The first optical layers 462, 466 and the second optical layers 464, 468 can be formed of materials that can minimize optical transmission losses as much as possible. Example materials can include a glass material, a plastic material and/or other suitable materials. An anti-reflective material may be applied to at least one surface of each of the first optical layers 462, 466 and the second optical layers 464, 468 to minimize reflection losses. The anti-reflective material can reduce undesirable reflections that may occur at the first optical layers 462, 466 and the second optical layers 464, 468. The type of anti-reflective material applied to the first optical layers 462, 466 and the second optical layers 464, 468 may vary for different wavelengths of the optical beam and/or an angle of incidence of the optical beam.

To further reduce residual reflection, the optical layer pairs 462 and 464, and 466 and 468 at the respective first and second end components 408f, 408s can be tilted in a similar manner as the first and second end components 208f, 208s of the gas cell 210A shown in FIG. 2A.

As shown in FIG. 4A, the first and second optical layers 462 and 464, and 466 and 468 are generally parallel to each other, and are also oriented at the respective end portion tilt angle 494s ($\theta_{t,s}$), 494f ($\theta_{t,f}$) relative to the axis 407 of the channel 406. The second optical frame 460s can be oriented at the end portion tilt angle 494s ($\theta_{t,s}$) relative to the axis 407 and the first optical frame 460f can be oriented at the end portion tilt angle 494f ($\theta_{t,f}$) relative to the axis 407. The end portion tilt angle 494s can be substantially equal in value to the end portion tilt angle 494f, but have mirror symmetry to each other so that the optical beam exiting from either ends of the channel does not deviate from the transmission path.

Residual reflection may still result from the transmission of the optical beams between the pairs of optical layers, such as the transmission of the first transmitted beam 50' between the second optical layer 468 and the first optical layer 466. An example optical transmission path involving residual reflection at the first optical layer 466 is described with reference to FIG. 5A.

Figure 5A:
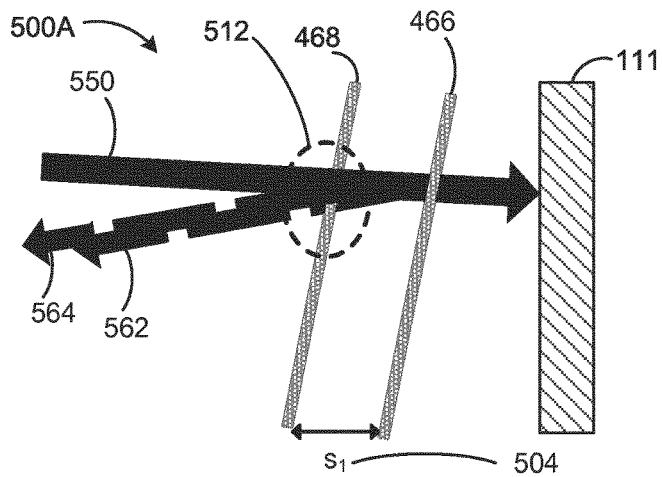
FIG. 5A shows an example transmission path at a portion of an example gas cell assembly in accordance with an example embodiment.

FIG. 5A shows an example transmission path 500A at a portion of an example gas cell assembly 10. The portion of the example gas cell assembly 10 shown in FIG. 5A includes a reflective surface 111 and the first optical layer 466 separated by a spacing ($s_1$) 504 from the second optical layer 468.

The example transmission path 500A shows a first transmitted beam 550 being transmitted towards the reflective surface 111 via the first and second optical layers 466 and 468. The example transmission path 500A shows that a residual beam 562 is produced from the interaction of the first transmitted beam 550 with the first optical layer 466, and a residual beam 564 is produced from the interaction of the first transmitted beam 550 and the second optical layer 468. With the configuration of the example gas cell assembly 10 shown in FIG. 5A, the residual beam 562 interferes with the first transmitted beam 550 at the second optical layer 468, and also interferes with the residual beam 564. The interference between the residual beams 562 and 564, and between the residual beam 562 and the first transmitted beam 550 can cause undesirable optical noise. The overlap of the residual beam 562, the residual beam 564 and the first transmitted beam 550 is shown generally as 512 in FIG. 5A.

Various characteristics of the gas cell assembly 10 can affect the degree of optical noise that the residual beams 562, 564 may cause. Example characteristics include a spacing between the first and second optical layers 466 and 468, a thickness of the first optical layer 466, a thickness of the second optical layer 468, and/or a diameter of the incident beam 50.

Figure 5B:
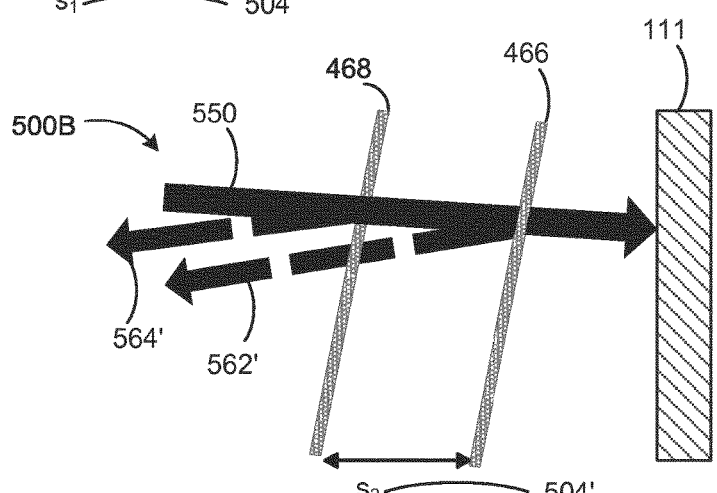
FIG. 5B shows another example transmission path at another example gas cell assembly.

FIG. 5B shows another example transmission path 500B at a portion of an example gas cell assembly 10. In FIG. 5B, the first optical layer 466 is separated from the second optical layer 468 by a spacing ($s_2$) 504'. The spacing ($s_2$) 504' is greater than the spacing ($s_1$) 504 in FIG. 5A. By increasing the spacing 504 between the first optical layer 466 and the second optical layer 468, the transmission path of the residual beam 562' does not overlap with the transmission path of the beam 550 at the second optical layer 468. The transmission path of the residual beam 562' also does not overlap with the transmission path of the residual beam 564'.

Figure 5C:
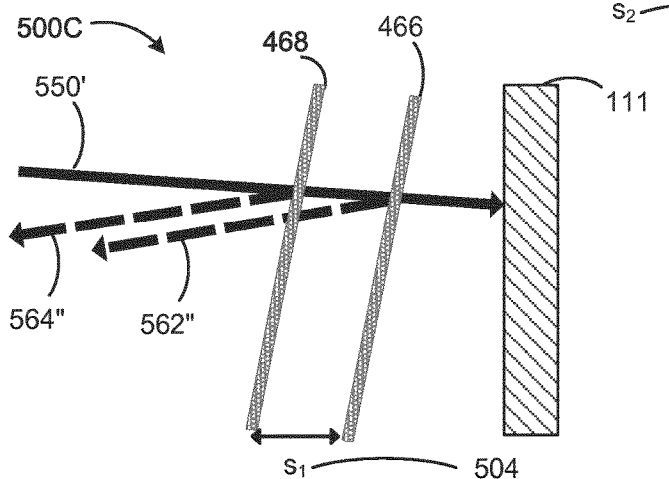
FIG. 5C shows another example transmission path at the example gas cell assembly shown in FIG. 5A.

FIG. 5C shows another example transmission path 500C at the portion of the example gas cell assembly 10 shown in FIG. 5A. Similar to the example shown in FIG. 5A, the first optical layer 466 is separated from the second optical layer 468 by the spacing ($s_1$) 504. The diameter of the first transmitted beam 550' in FIG. 5C is narrower than the diameter of the first transmitted beam 550 in FIG. 5A. As shown in FIG. 5C, due to the narrower diameter of the first transmitted beam 550', the transmission path of the residual beam 562" does not overlap with the transmission path of the first transmitted beam 550' at the second optical layer 468 even though the first optical layer 466 is separated from the second optical layer 468 by the spacing ($s_1$) 504. Similarly, the residual beams 562" and 564" also do not interfere with each other due to the narrower diameter of the first transmitted beam 550'.

Referring again to FIGS. 1B and 4A, the first and second optical layers 466 and 468 are not parallel to the reflective surface 111. As a result, the transmission path of the reflected beam 52 from the reflective surface 111 will not be parallel to the transmission path of the second transmitted beam 50" (see FIG. 1B, for example). As will be described with reference to FIGS. 6A to 6C, various characteristics of the gas cell assembly 100A, 100B can affect whether the transmission path of the reflected beam 52 overlaps with the transmission path of the second transmitted beam 50" at the first optical layer 466. The various example characteristics can include a size of a spacing between the first and second optical layers 466 and 468, a thickness of the first optical layer 466, a thickness of the second optical layer 468, and/or a diameter of the incident beam 50.

Figure 6A:
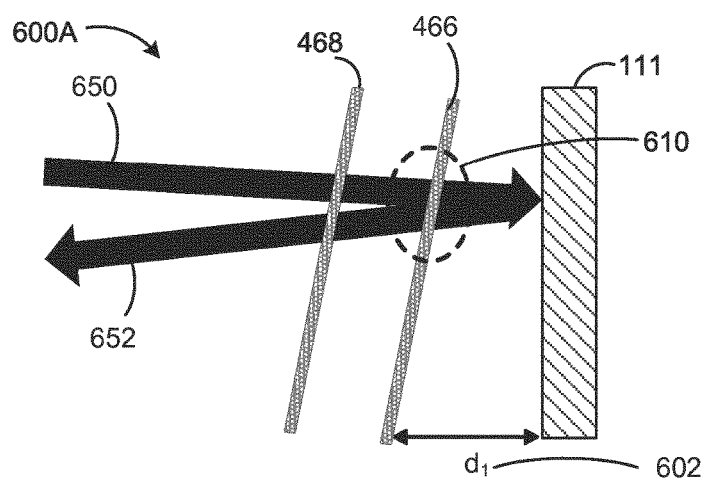
FIG. 6A shows an example transmission path at a portion of an example gas cell assembly in accordance with an example embodiment.

FIG. 6A shows an example transmission path 600A at a portion of an example gas cell assembly 10. In FIG. 6A, the reflective surface 111 is positioned at a distance ($d_1$) 602 from the first optical layer 466. The distance ($d_1$) is measured between the farthest points of the reflective surface 111 and the first optical layer 466.

In the transmission path 600A shown in FIG. 6A, the first transmitted beam 650 is transmitted from the channel 406 via the first and second optical layers 466 and 468 towards the reflective surface 111. The reflective surface 111 reflects the first transmitted beam 650 to produce a reflected beam 652, and directs the reflected beam 652 towards the first optical layer 466. As shown in FIG. 6A, the transmission path of the reflected beam 652 is not parallel to the transmission path of the first transmitted beam 650. Instead, the transmission paths of the beams 650 and 652 interfere with each other at the first optical layer 466. The overlap of the beams 650 and 652 is shown generally as 610.

Figure 6B:
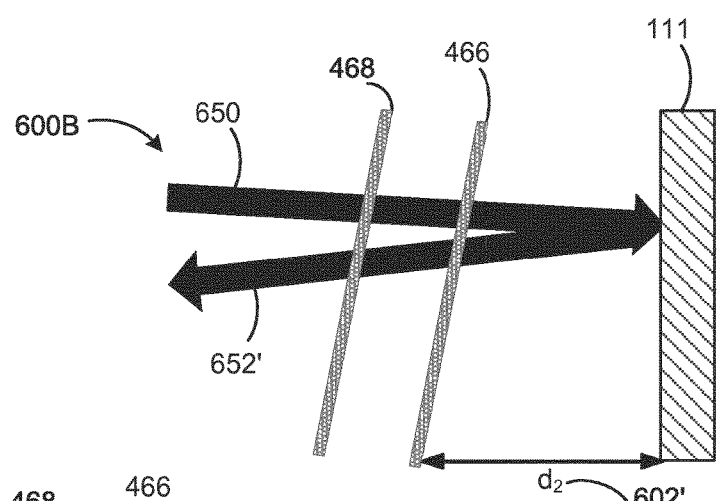
FIG. 6B shows an example transmission path at another example gas cell assembly.

FIG. 6B shows another example transmission path 600B at a portion of another example gas cell assembly 10. In FIG. 6B, the reflective surface 111 is positioned at a distance ($d_2$) 602' from the first optical layer 466 instead of the distance ($d_1$) 602 in the example shown in FIG. 6A. The distance ($d_2$) 602' is greater than the distance ($d_1$) 602. By increasing the distance 602 between the first optical layer 466 and the reflective surface 111, the transmission paths of the beams 652' and 650 do not overlap at the first optical layer 466.

Figure 6C:
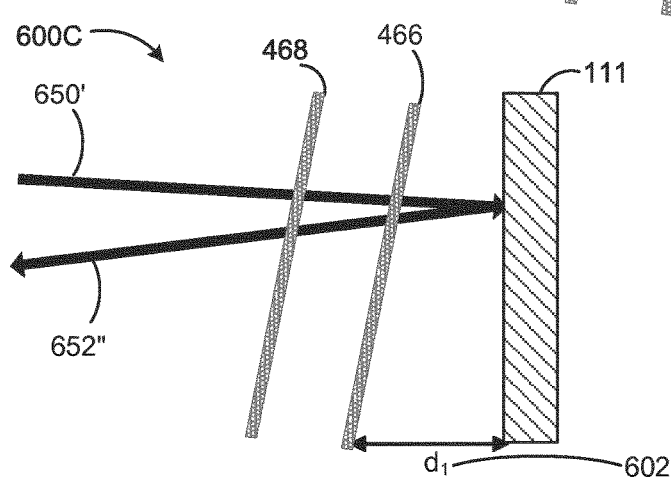
FIG. 6C shows another example transmission path at the example gas cell assembly shown in FIG. 6A.

FIG. 6C shows another example transmission path 600C at the gas cell assembly 10 shown in FIG. 6A. In the embodiment shown in FIG. 6C, the diameter of the first transmitted beam 650' is narrower than the diameter of the first transmitted beam 650 shown in FIG. 6A. As a result of the narrower diameter of the first transmitted beam 650', the transmission paths of the reflected beam 652" and the first transmitted beam 650' do not overlap at the first optical layer 466 even though the reflective surface 111 is located at the distance ($d_1$) 602 from the first optical layer 466.

Figure 4B:
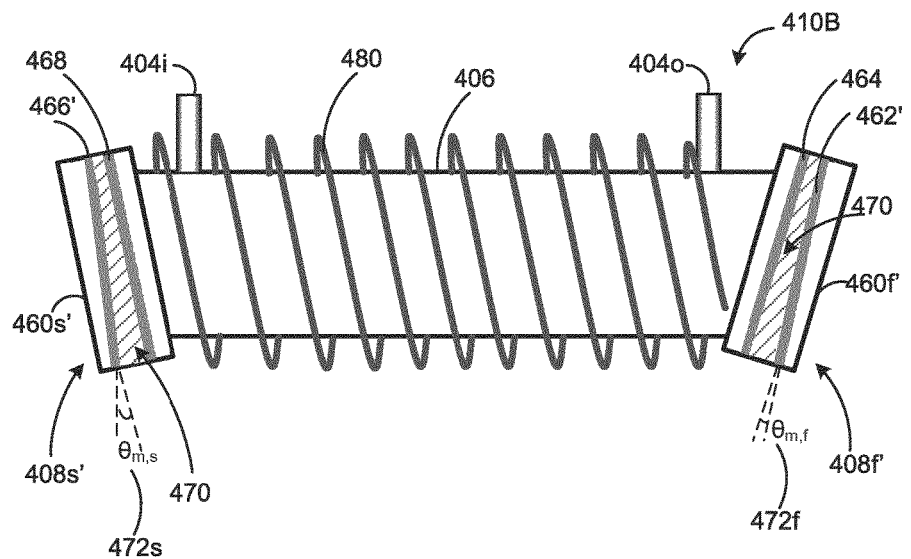
FIG. 4B shows the example gas cell in FIG. 4A in accordance with another example embodiment.

FIG. 4B shows an example gas cell 410B. The example gas cell 410B is similar to the gas cell 410A except for the configuration of the pairs of optical layers 462' and 464, and 466' and 468.

The first end component 408f' of the gas cell 410B includes a first optical layer 462' and the second optical layer 464. The first optical layer 462' is positioned relative to the second optical layer 464 at an optical layer tilt angle 472f ($\theta_{m,f}$). A first optical frame 460f' can facilitate the orientation of the first optical layer 462' with respect to the second optical layer 464.

Similarly, the second end component 408s' includes a first optical layer 466' that is also positioned relative to the second optical layer 468 at an optical layer tilt angle 472s ($\theta_{m,s}$). The optical layer tilt angle 472f can have the same value as the optical layer tilt angle 472s but the optical layer tilt angle 472f has mirror symmetry with the optical layer tilt angle 472s. A second optical frame 460s' can also facilitate the orientation of the first optical layer 466' with respect to the second optical layer 468.

The orientation of the first optical layer 462' with respect to the second optical layer 464 at the optical layer tilt angle 472f, and the orientation of the first optical layer 466' with respect to the second optical layer 468 at the optical layer tilt angle 472s can help to reduce any optical noise that may result from residual reflections produced between the first optical layer 462' and the second optical layer 464, and between the first optical layer 466' and the second optical layer 468. By tilting the first optical layer 462', 466' with respect to the second optical layer 464, 468, the residual reflections that may be produced by the first optical layers 462', 466' and second optical layers 464, 468 will not travel parallel to the incident beam 50 and as a result, optical noise can be reduced.

As described with reference to FIGS. 6A to 6C, various characteristics of the gas cell assembly 10, such as the size of the spacing between each pair of first optical layer 462, 466 and second optical layer 464, 468, a thickness of the first optical layer 462, 466, a thickness of the second optical layer 464, 468, and a diameter of the incident beam 50, can affect the optical transmission path within the gas cell. Since the optical layer tilt angles 472f, 472s can also vary the optical transmission path, the value of the optical layer tilt angles 472f, 472s can be varied with the characteristics of the gas cell assembly 10.

In some embodiments, the second optical layer 464, 468 may instead be tilted at the respective optical layer tilt angles 472f, 472s relative to the first optical layer 462', 466'. In some embodiments, both the first optical layers 462, 466 and the second optical layers 464, 468 may be tilted with respect to each other and the longitudinal axis of the respective optical frames 460f, 460s.

In some embodiments, each of the optical layer tilt angles 472f, 472s may be greater than 0 degrees and below or equal to 10 degrees. Other values for the optical layer tilt angles 472f, 472s may be used.

FIG. 7A is a cross-sectional view of another example gas cell 710A.

The gas cell 710A is generally similar to the gas cell 410A shown in FIG. 4A except for the first and second end components 708f and 708s. In FIG. 7A, the first end component 708f includes the first optical frame 460f containing the first and second optical layers 462 and 464, and a baffle 790f mounted thereon, and the second end component 708s includes the second optical frame 460s containing the first and second optical layers 466 and 468, and a baffle 790s mounted thereon. As described with respect to FIG. 2A, baffles 790f, 790s can help to stabilize the temperature between the channel 406 and the optically transparent portions, such as optical layers 462, 464, 466 and 468. With the baffles 790f, 790s, the temperature of the first optical layers 462 and 466 can be regulated since they are not directly exposed to the test environment.

Also, the baffles 790f, 790s can help to minimize the temperature variation within the space 470 between each pair of optical layers 462 and 464, and 466 and 468. The temperature within the space 470 between each pair of optical layers 462 and 464, and 466 and 468 can be characterized by a temperature gradient that decreases in value from the second optical layers 464, 468 towards the first optical layers 462, 466. Baffles 790f, 790s can reduce the temperature variation within the space 470. As a result, the likelihood for the formation of cold and hot spots at the first optical layers 462, 466 can be minimized.

FIG. 7B shows another example gas cell 710B.

Similar to gas cell 710A shown in FIG. 7A, the first and second end components 708f' and 708s' includes baffles 790f, 790s mounted to the respective optical frames 460f, 460s. Unlike the gas cell 710A, the gas cell 710B includes a temperature varying material coupled to each of the baffles 790f, 790s. The temperature varying material shown in FIG. 7B is a temperature varying coil 782. Like the temperature varying coil 282 shown in FIG. 2B, the temperature varying coil 782 can help to stabilize the temperature at the pairs of optical layers 462 and 464, and 466 and 468 with respect to the interior of the channel 406. The temperature varying coil 782 can also reduce the degree of variation at the temperature gradient within the space 470.

Like the temperature varying coils 280, 282 shown in FIG. 2B, the temperature varying coils 780, 782 can be controlled to effect a generally uniform temperature at the pairs of optical layers 762 and 764, and 766 and 768, and the interior of the channel 406. For example, the temperature varying coil 780 and the temperature varying coil 782 can be controlled to provide the same temperature to the respective components of the gas cell 710B. In some other embodiments, depending on the temperature measured at each pair of optical layers 762 and 764, and 766 and 768, and the channel 406, the temperature of each of the temperature varying coils 780 and 782 may be controlled to provide different temperatures at the respective components of the gas cell 710B in order to provide an overall uniform temperature at the gas cell 710B.

Figure 7C:
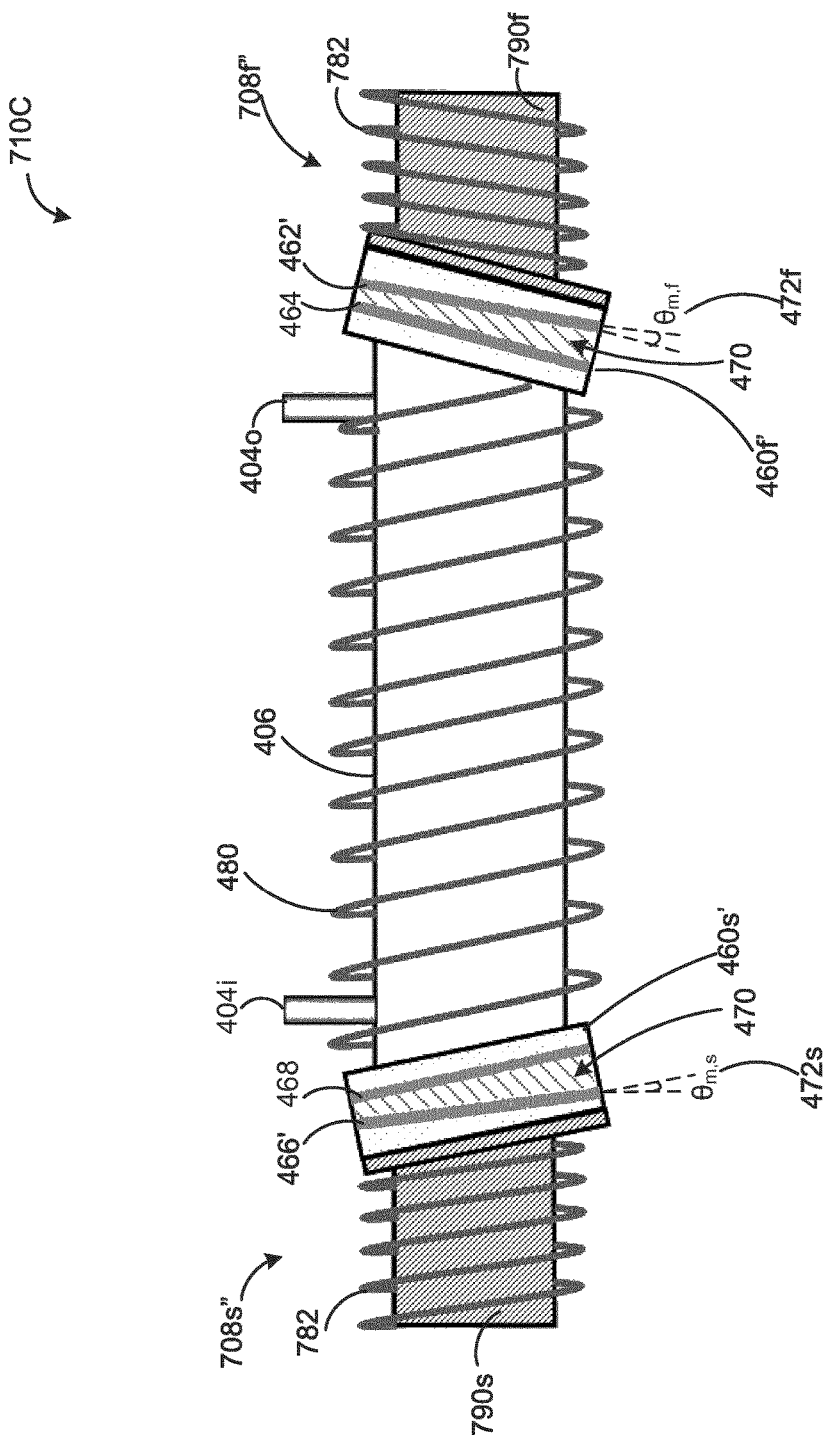
FIG. 7C shows the example gas cell in FIG. 7A in accordance with yet another example embodiment.

FIG. 7C shows another example gas cell 710C.

The gas cell 710C is generally similar to the gas cell 410B shown in FIG. 4B except for the first and second end components 708f" and 708s", respectively. In FIG. 7B, the first end component 708f" includes the first optical frame 460f' containing the first and second optical layers 462' and 464 and a baffle 790f mounted thereon, and the second end component 708s" includes the second optical frame 460s' containing the first and second optical layers 466' and 468, and a baffle 790s mounted thereon. As described with reference to FIG. 4B, the first optical layer 462' is positioned relative to the second optical layer 464 at the optical layer tilt angle 472f ($\theta_{m,f}$), and the first optical layer 466' is positioned relative to the second optical layer 468 at the optical layer tilt angle 472s ($\theta_{m,s}$). In the example shown in FIG. 7C, each of the baffles 790f, 790s is coupled with the temperature varying coil 782. It will be understood that some embodiments of the gas cell 710C may include baffles 790f, 790s that are not coupled with the temperature varying coil 782.

FIG. 8 is a cross-sectional view of another example gas cell 810.

The gas cell 810 includes a channel 806 with an inlet 804i and an outlet 804o. A temperature varying coil 880 surrounds the channel 806 for regulating the temperature within the channel 806. The channel 806 is enclosed by a first end component 808f and a second end component 808s. The first and second end components 808f, 808s are securably and removably mounted to the respective ends of the channel 806 with a coupling 809f, 809s. The coupling 809f, 809s may be a threaded coupling or other similar type of couplings.

Similar to the gas cells 710A, 710B, and 710C, the gas cell 810 includes a pair of optical layers at each of the first and second end components 808f and 808s, respectively. The first end component 808f includes a first optical layer 862 and a second optical layer 864 that is separated from the first optical layer 862 by a space 870, and the second end component 808s includes a first optical layer 866 and a second optical layer 868 that is separated from the first optical layer 866 by a space 870. However, unlike the gas cells 710A, 710B, and 710C, the pairs of optical layers 862, 864 and 866, 868 are positioned inwardly within the gas cell 810.

As described with reference to the gas cell 310, positioning the pairs of optical layers 862, 864 and 866, 868 inwardly within the channel 806 can shield the pairs of optical layers 862, 864 and 866, 868 from being directly engaged with the external environment of the gas cell 810. As a result, the temperature at the pairs of optical layers 862, 864 and 866, 868 are less susceptible to the temperature of the external environment. Also, the temperature of the pairs of optical layers 862, 864 and 866, 868 can benefit from being regulated by the internal temperature of the channel 806 and/or the temperature varying coil 880 surrounding the channel 806.

The position of the pairs of optical layers 862, 864 and 866, 868 within the length of the channel 806 can vary with the overall length of the channel 806 and the desired path length for the overall optical transmission. Similar to embodiment shown in FIG. 3, the position at which the pairs of optical layers 862, 864 and 866, 868 are mounted within the channel 806 can vary with the type of absorption spectroscopy to be conducted. When less sensitive data measurements are satisfactory, a shorter path length can be used for absorption spectroscopy and so, the pairs of optical layers 862, 864 and 866, 868 can be mounted further within the channel 806 in order to maximize the temperature regulation of the pairs of optical layers 862, 864 and 866, 868. However, when a high level of sensitivity for the data is required, a longer path length is desired and so, the pairs of optical layers 862, 864 and 866, 868 can be mounted closer to either ends of the channel 806 in order to maximize the path length.

As shown in FIG. 8, a first extending member 890f can mount the pairs of optical layers 862, 864 inwardly with the channel 806 and a second extending member 890s can mount the pairs of optical layers 866, 868 inwardly within the channel 806. Each of the extending members 890f, 890s has a respective first member end 892f, 894f that is mounted to the respective end of the channel 806 via the coupling 809f, 809s. The extending members 890f, 890s also has a respective second member end 892s, 894s that extends inwardly within the channel 806. The pairs of optical layers 862, 864 and 866, 868 are mounted to the respective second members ends 892s, 894s.

An optical frame, such as 860f and 860s, can contain the respective pairs of optical layers 862, 864 and 866, 868. As shown in FIG. 8, the optical frames 860f and 860s are mounted to the second member end 892s, 894s. In some other embodiments, the pairs of optical layers 862, 864 and 866, 868 can be mounted directly to the second member end 892s, 894s without the optical frames 860f and 860s.

Baffles may be used as the extending members 890f, 890s, in some embodiments.

Various embodiments have been described herein by way of example only. Various modification and variations may be made to these example embodiments without departing from the spirit and scope of the invention, which is limited only by the appended claims.

What is claimed is:

1. A gas cell for absorption spectroscopy, the gas cell comprising:
   a channel providing at least a passage from a first end to a second end, the channel comprising an inlet for receiving a gas sample from a gas source and an outlet for releasing the gas sample from the gas cell, the first end being substantially opposite from the second end;
   a first end component coupled to the first end and a second end component coupled to the second end, each of the first end component and the second end component comprising;
   a mounting end coupled to the respective first end and second end of the channel; an extending member coupled to the respective mounting end and extending inwardly within the channel from the respective mounting end; and
   an optical frame coupled to the respective extending member inwardly within the channel and containing an optically transparent portion, the optical frame being spaced from the respective mounting end, and the extending member defining a space from the optical frame to an opening defined by the respective mounting end such that the space is exposed to an external environment of the gas cell;
   wherein the optically transparent portion coupled to the first end component is positioned inwardly within the channel and positioned to receive an incident beam from an optical source into the channel via the opening defined by the mounting end coupled to the first end; and
   the optically transparent portion coupled to the second end component is positioned inwardly within the channel and positioned to permit optical transmission into and out of the channel; and
   each of the optically transparent portions is oriented at a tilt angle relative to the respective mounting end; and
   wherein at least one of the optically transparent portions of the first end component and the second end component comprises two optical layers; and
   wherein a value of the optical layer tilt angle varies with at least one of a spacing size between the first and second optical layers, a thickness of the first optical layer, a thickness of the second optical layer, and a diameter of the incident beam.

2. The gas cell of claim 1, wherein each of the first end component and the second end component comprises a baffle.

3. The gas cell of claim 1, wherein a temperature varying material is coupled to the channel.

4. The gas cell of claim 1, wherein at least one surface of the optically transparent portions of the first end component and the second end component is applied with an anti-reflective coating.

5. The gas cell of claim 1, wherein each of the first end component and the second end component is removably mounted to the channel.

6. The gas cell of claim 5, wherein each of the first end component and the second end component is removably mounted to the channel with a threaded coupling.

7. An absorption spectroscopy system comprising:
   an optical source for generating an incident beam;
   a gas cell having:
   a channel providing at least a passage from a first end to a second end, the channel comprising an inlet for receiving a gas sample from a gas source and an outlet for releasing the gas sample from the gas cell, the first end being substantially opposite from the second end;
   a first end component coupled to the first end and a second end component coupled to the second end, each of the first end component and the second end component comprising:
   a mounting end coupled to the respective first end and second end of the channel;
   an extending member coupled to the respective mounting end and extending inwardly within the channel from the respective mounting end; and
   an optical frame coupled to the respective extending member inwardly within the channel and containing an optically transparent portion, the optical frame being spaced from the respective mounting end, and the extending member defining a space from the optical frame and an opening defined by the respective mounting end such that the space is exposed to an external environment of the gas cell;
   wherein the first optically transparent portion coupled to the first end component is positioned inwardly within the channel and positioned to receive the incident beam from the optical source into the channel via the opening defined by the mounting end coupled to the first end;
   the optically transparent portion coupled to the second end component is positioned inwardly within the channel and positioned to permit optical transmission into and out of the channel; and
   each of the optically transparent portions is oriented at a tilt angle relative to the respective mounting end; and
   wherein at least one of the optically transparent portions of the first end component and the second end component comprises two optical layers; and
   wherein a value of the optical layer tilt angle varies with at least one of a spacing size between the first and second optical layers, a thickness of the first optical layer, a thickness of the second optical layer, and a diameter of the incident beam; and
   a detector positioned relative to the channel for receiving a version of the incident beam and transmitting a data signal corresponding to the version of the incident beam to an absorption spectroscopy analyzer.

8. The gas cell of claim 1, wherein a first optical layer of the two optical layers is substantially parallel with a second optical layer of the two optical layers.

9. The gas cell of claim 1, wherein a first optical layer of the two optical layers is positioned relative to a second optical layer of the two optical layers at an optical layer tilt angle.

10. The gas cell of claim 1, wherein the value of the optical layer tilt angle is greater than 0 degrees and less than or equal to 10 degrees.

11. The gas cell of claim 1, wherein a space between the first two optical layers is vacuum sealed.

12. The gas cell of claim 1, wherein a space between the first two optical layers is filled with an insulation material characterized by a low thermal conductivity.

13. The gas cell of claim 12, wherein the insulation material comprises a gaseous material optically transparent to the incident beam.

14. The gas cell of claim 2, wherein a temperature varying material is coupled to each baffle.

15. The gas cell of claim 1, wherein:
an interior surface of the optically transparent portion coupled to the first end component is exposed to the gas sample, and an exterior surface of the optically transparent portion coupled to the first end component is unobstructed to receive the incident beam.

\* \* \* \* \*